(12) United States Patent
Rieker et al.

(10) Patent No.: US 8,454,588 B2
(45) Date of Patent: Jun. 4, 2013

(54) METHOD AND APPARATUS TO PREVENT ESOPHAGEAL DAMAGE

(75) Inventors: Gregory Brian Rieker, Palo Alto, CA (US); Venkatesh Vasudevan, Stanford, CA (US); Uday N. Kumar, San Francisco, CA (US); William Croisettier, Stanford, CA (US); William Bragg, Palo Alto, CA (US); Gary Mekikian, La Canada, CA (US); Richard Ian Whyte, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1077 days.

(21) Appl. No.: 11/724,791

(22) Filed: Mar. 16, 2007

(65) Prior Publication Data

US 2008/0033415 A1 Feb. 7, 2008

Related U.S. Application Data

(60) Provisional application No. 60/782,827, filed on Mar. 17, 2006.

(51) Int. Cl.
*A61B 18/02* (2006.01)

(52) U.S. Cl.
USPC .............................. 606/23; 606/191

(58) Field of Classification Search
USPC ........... 606/1, 32, 34, 41, 191, 22–23, 25–26; 600/146–151, 139, 144, 145, 120, 380; 607/112, 607/129, 133, 135
See application file for complete search history.

(56) References Cited

U.S. PATENT DOCUMENTS

| 3,773,034 | A | | 11/1973 | Burns et al. |
| 4,960,411 | A | | 10/1990 | Buchbinder |
| 5,090,956 | A | | 2/1992 | McCoy |
| 5,125,895 | A | | 6/1992 | Buchbinder et al. |
| 5,170,803 | A | * | 12/1992 | Hewson et al. ............... 607/124 |

(Continued)

FOREIGN PATENT DOCUMENTS

EP 0694284 A1 1/1996

OTHER PUBLICATIONS

Benussi et al.; A tailored anatomical approach to prevent complications during left atrial ablation; Ann Thorac Surg; vol. 75; pp. 1979-1981; 2003.

(Continued)

*Primary Examiner* — Michael Peffley
*Assistant Examiner* — Thomas Giuliani
(74) *Attorney, Agent, or Firm* — Shay Glenn LLP

(57) ABSTRACT

An apparatus for moving the esophagus includes an elongate body having a distal tip, a controlled curvature section, and a flexible section. A handle is coupled to the flexible section to adjust the curvature of the controlled curvature section. The length of the controlled curvature section is less than the length of the thoracic portion of the esophagus. Further, a method of adjusting the curvature of the esophagus during a therapeutic procedure in a treatment area outside of the esophagus includes positioning within the esophagus an elongate body having a distal tip, a controlled curvature section, and a flexible section and adjusting the curvature of the controlled curvature section to increase the distance between the esophagus and a treatment area outside of the esophagus.

12 Claims, 21 Drawing Sheets

U.S. PATENT DOCUMENTS

| | | | | |
|---|---|---|---|---|
| 5,315,996 | A * | 5/1994 | Lundquist | 600/374 |
| 5,397,304 | A * | 3/1995 | Truckai | 604/528 |
| 5,758,656 | A * | 6/1998 | Schroeder | 600/585 |
| 5,957,863 | A | 9/1999 | Koblish et al. | |
| 6,067,990 | A | 5/2000 | Kieturakis | |
| 6,073,052 | A * | 6/2000 | Zelickson et al. | 607/100 |
| 6,259,938 | B1 * | 7/2001 | Zarychta et al. | 600/380 |
| 7,621,908 | B2 * | 11/2009 | Miller | 606/32 |
| 2002/0007125 | A1 | 1/2002 | Hickey | |
| 2003/0154986 | A1 | 8/2003 | Fariss et al. | |
| 2004/0147801 | A1 * | 7/2004 | Kugler et al. | 600/12 |
| 2004/0147828 | A1 * | 7/2004 | Gibson | 600/374 |
| 2004/0171942 | A1 | 9/2004 | Ackerman et al. | |
| 2004/0210281 | A1 * | 10/2004 | Dzeng et al. | 607/96 |
| 2005/0043601 | A1 | 2/2005 | Kilcoyne et al. | |
| 2005/0107829 | A1 * | 5/2005 | Edwards et al. | 607/2 |
| 2005/0222652 | A1 | 10/2005 | Mori | |
| 2005/0228504 | A1 * | 10/2005 | Demarais | 623/23.65 |
| 2007/0118097 | A1 * | 5/2007 | Miller | 606/1 |
| 2007/0225701 | A1 * | 9/2007 | O'Sullivan | 606/41 |

OTHER PUBLICATIONS

Berjano et al.; A cooled intraesophageal balloon to prevent thermal injury during endocardial surgical radiofrequency ablation of the left atrium: a finite element study; Phys Med Biol; vol. 50; pp. N269-N279; 2005.

Calkins et al.; Catheter ablation of accessory pathways, atrioventricular nodal reentrant tachycardia, and the atrioventricular junction; Circulation; vol. 99; pp. 262-270; 1999.

Callans et al.; Efficacy of repeat pulmonary vein isolation procedures in patients with recurrent atrial fibrillation; J Cardiovasc Electrophysiol; vol. 15; pp. 1050-1055; Sep. 2004.

Cappato et al.; Worldwide survey on the methods, efficacy, and safety of catheter ablation for human atrial fibrillation; Circulation; vol. 111; pp. 1100-1105; 2005.

Chao, H.H. (Comprehensive Digestive Disease Center); Endoscopic Ultrasound: a view from within; 2 pgs.; printed/accessed Sep. 13, 2010.

Doll et al.; Esophageal perforation during left atrial radiofrequency ablation: is the risk too high?; J. Thorac Cardiovasc Surg; vol. 125; pp. 836-842; Apr. 2003.

Gerstenfeld et al.; Mechanisms of organized left atrial tachycardias occuring after pulmonary vein isolation; Circulation; vol. 110; pp. 1351-1357; 2004.

Go et al.; Prevalence of diagnosed atrial fibrillation in adults; JAMA; vol. 285; No. 18; pp. 2370-2375; May 9, 2001.

Goldberg et al.; Atrial fibrillation ablation leads to long-term improvement of quality of life and reduced utilization of healthcare resources; Journal of Interventional Cardiac Electrophysiology; vol. 8; pp. 59-64; 2003.

Good et al.; Movement of the esophagus during left atrial catheter ablation for atrial fibrillation; J Am Coll Cardiol; vol. 46; No. 11; pp. 2107-2110; 2005.

Gress et al.; Endoscopic ultrasonograpy, fine-needle aspiration biopsy guided by endoscopic ultrasonography, and computed tomography in the preoperative staging of non-small-cell lung cancer; Ann Intern Med; vol. 127; pp. 604-612; 1997.

Haïssaguerre et al.; Electrophysiological breakthroughs from the left atrium to the pulmonary veins; Circulation; vol. 102; pp. 2463-2465; 2000.

Haïssaguerre et al.; Spontaneous initiation of atrial fibrillation by ectopic beats originating in the pulmonary veins; The New England Journal of Medicine; vol. 339; No. 10; pp. 659-666; 1998.

Health Research International; Transcatheter AF Ablation, Patient and Market Forecast 2001-2010; 1 pg.; 2002.

Jhala et al.; Endoscopic ultrasound-guided fine-needle aspiration; Am J Clin Pathol; vol. 120; pp. 351-367; 2003.

Kottkamp et al.; Topographic variability of the esophageal left atrial relation incluencing ablation lines in patients with atrial fibrillation; J. Cardiovasc. Electrophysiol.; vol. 16; pp. 146-150; Feb. 2005.

Lemola et al.; Computed tomographic analysis of the anatomy of the left atrium and the esophagus; Circulation; vol. 110; pp. 3655-3660; 2004.

Lloyd-Jones et al.; Lifetime risk for development of atrial fibrillation; Circulation; vol. 110; pp. 1042-1046; 2004.

Marine et al.; Catheter ablation therapy for atrial fibrillation; Progress in Cardiovascular Diseases; vo. 48; No. 3; pp. 178-192; Nov./Dec. 2005.

Needle aspiration biopsy; Wikipedia; 4 pgs.; printed/accessed Sep. 13, 2010.

Oral, H.; Pulmonary vein occlusion/stenosis after pulmonary vein ablation for atrial fibrillation; J. Cardiovasc. Electrophysiol.; vol. 14; pp. 371-372; Apr. 2003.

Pappone et al.; Atrio-esophageal fistula as a complication of percutaneous transcatheter ablation of atrial fibrillation; Circulation; vol. 109; pp. 2724-2726; 2004.

Pappone et al.; Mortality, morbidity, and quality of life after circumferential pulmonary vein ablation for atrial fibrillation: outcomes from a controlled nonrandomized long-term study; J. Am. Coll. Cardiol.; vol. 42; pp. 185-197; Jul. 16, 2003.

Pappone et al.; Prevention of iatrogenic atrial tachycardia after ablation of atrial fibrillation; vol. 110; pp. 3036-3042; 2004.

Peters et al.; Atrial fibrillation: strategies to control, combat, and cure; The Lancet; vol. 359; pp. 593-603; Feb. 16, 2002.

Pollak et al.; Novel imaging techniques of the esophagus enhancing safety of left atrial ablation; J Cardiovasc Electrophysiol; vol. 16; pp. 244-248; Mar. 2005.

Redfearn et al.; Esophageal temperature monitoring during radiofrequency ablation of atrial fibrillation; J Cardiovasc Electrophysiol; vol. 16; pp. 589-593; Jun. 2005.

Sanchez-Quintana et al.; Anatomic relations between the esophagus and left atrium and relevance for ablation of atrial fibrillation; Circulation; vol. 112; pp. 1400-1405; 2005.

Shah et al.; Acute pyloric spasm and gastric hypomotility; J Am Coll Cardiol; vol. 46; pp. 327-330; 2005.

Silvestri et al.; Endoscopic ultrasound with fine-needle aspiration in the diagnosis and staging of lung cancer; Ann Thorac Surg; vol. 61; pp. 1441-1445; 1996.

Sosa et al.; Left atrial-esophageal fistula complicating radiofrequency catheter ablation of atrial fibrillation; J. Cardiovasc Electrophysiol; vol. 16; pp. 249-250; Mar. 2005.

Yamane et al.; Visualization of the esophagus throughout left atrial catheter ablation for abrial fibrillation; J Cardiovasc Electrophysiol; vol. 17; p. 105; Jan. 2006.

Cummings et al.; Assessment of temperature, proximity, and course of the esophagus during radiofrequency ablation within the left atrium; Circulation; vol. 112; pp. 459-464; 2005.

Hornero et al.; Esophageal temperature during radiofrequency-catheter ablation of left atrium: a three-dimensional computer modeling study; J Cardiovasc Electrophysiol; vol. 17; pp. 405-410; Apr. 2006.

* cited by examiner

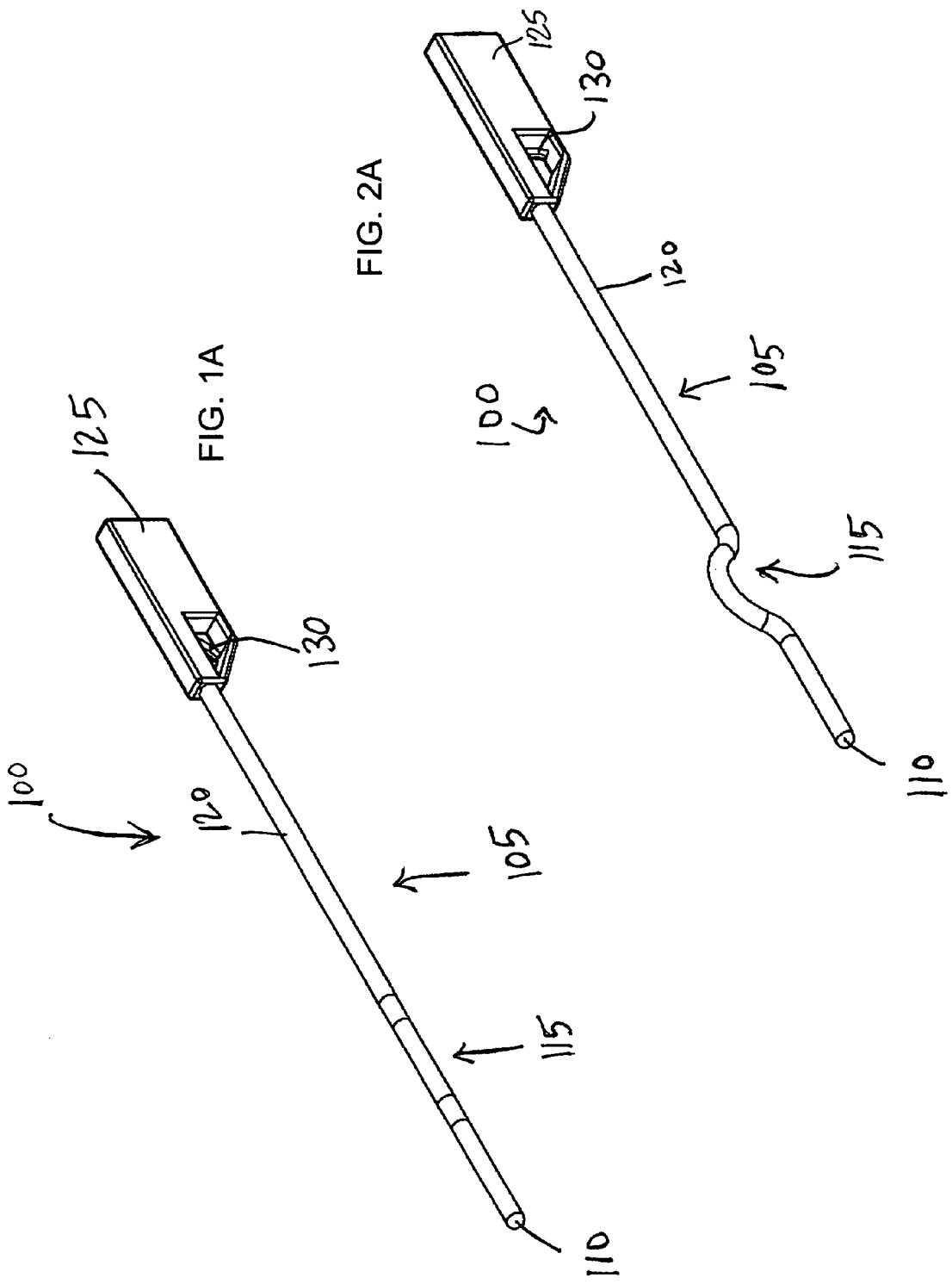

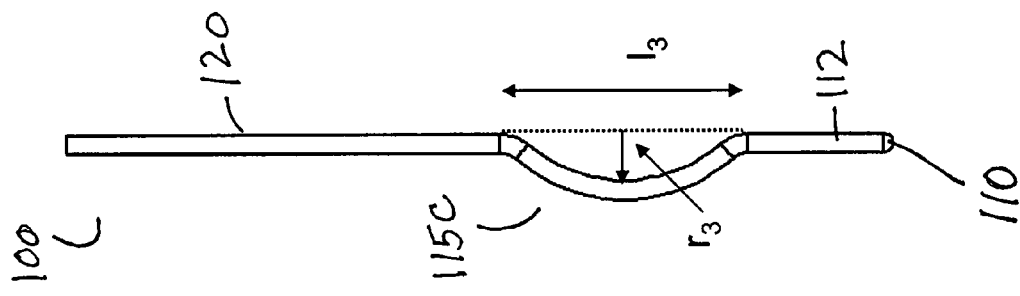
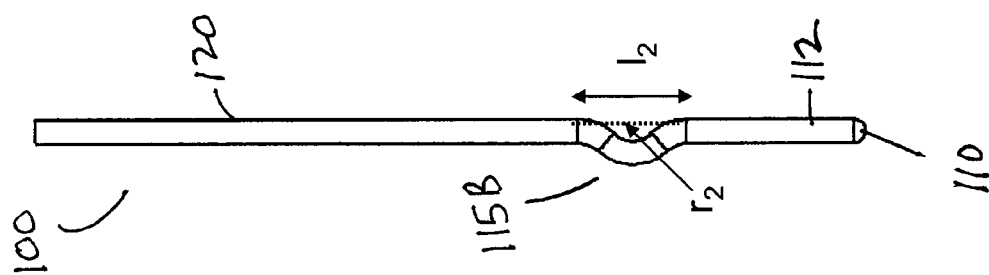
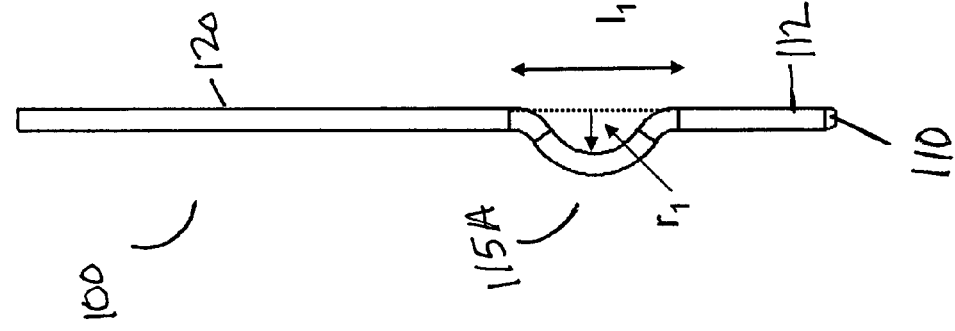

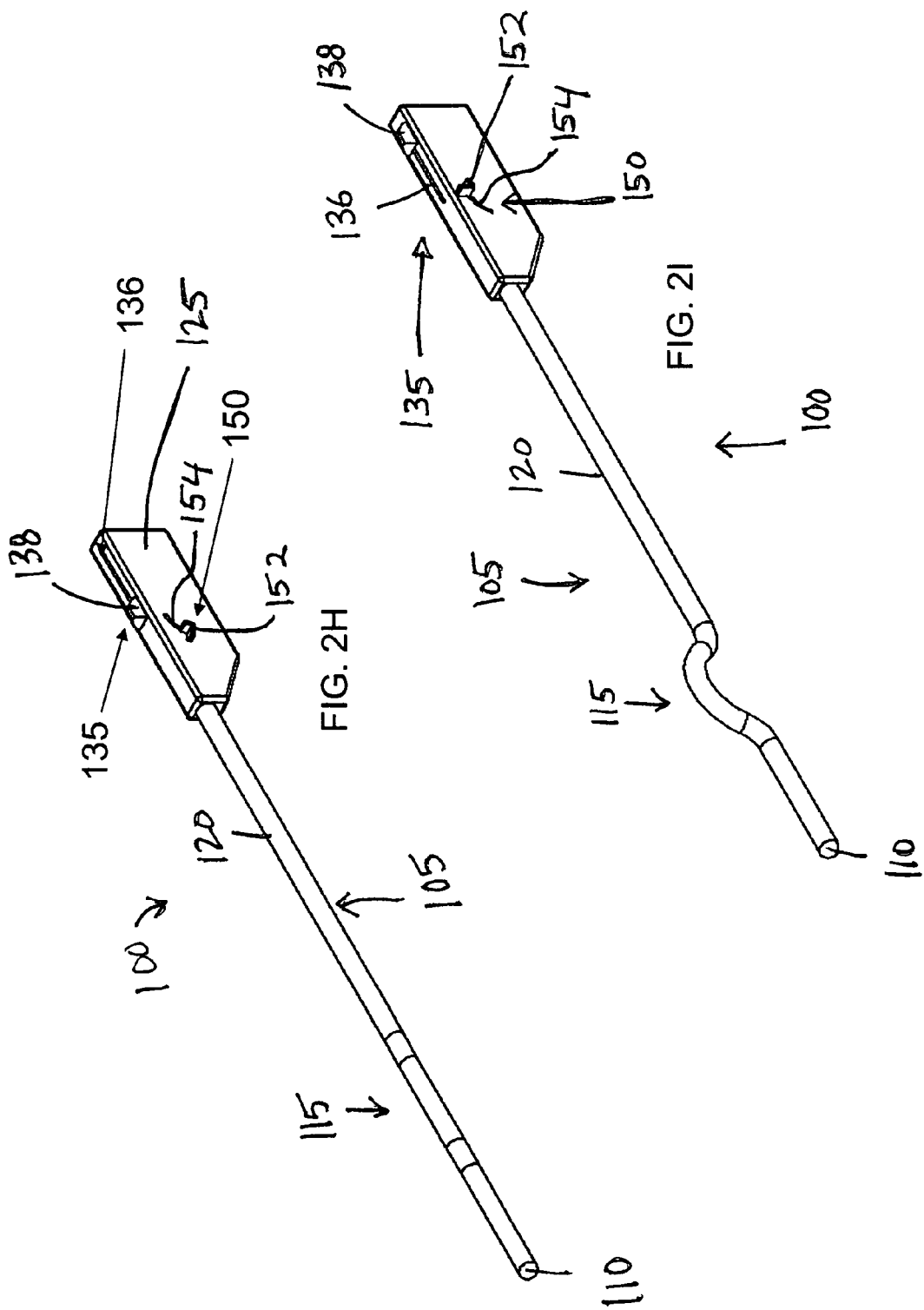

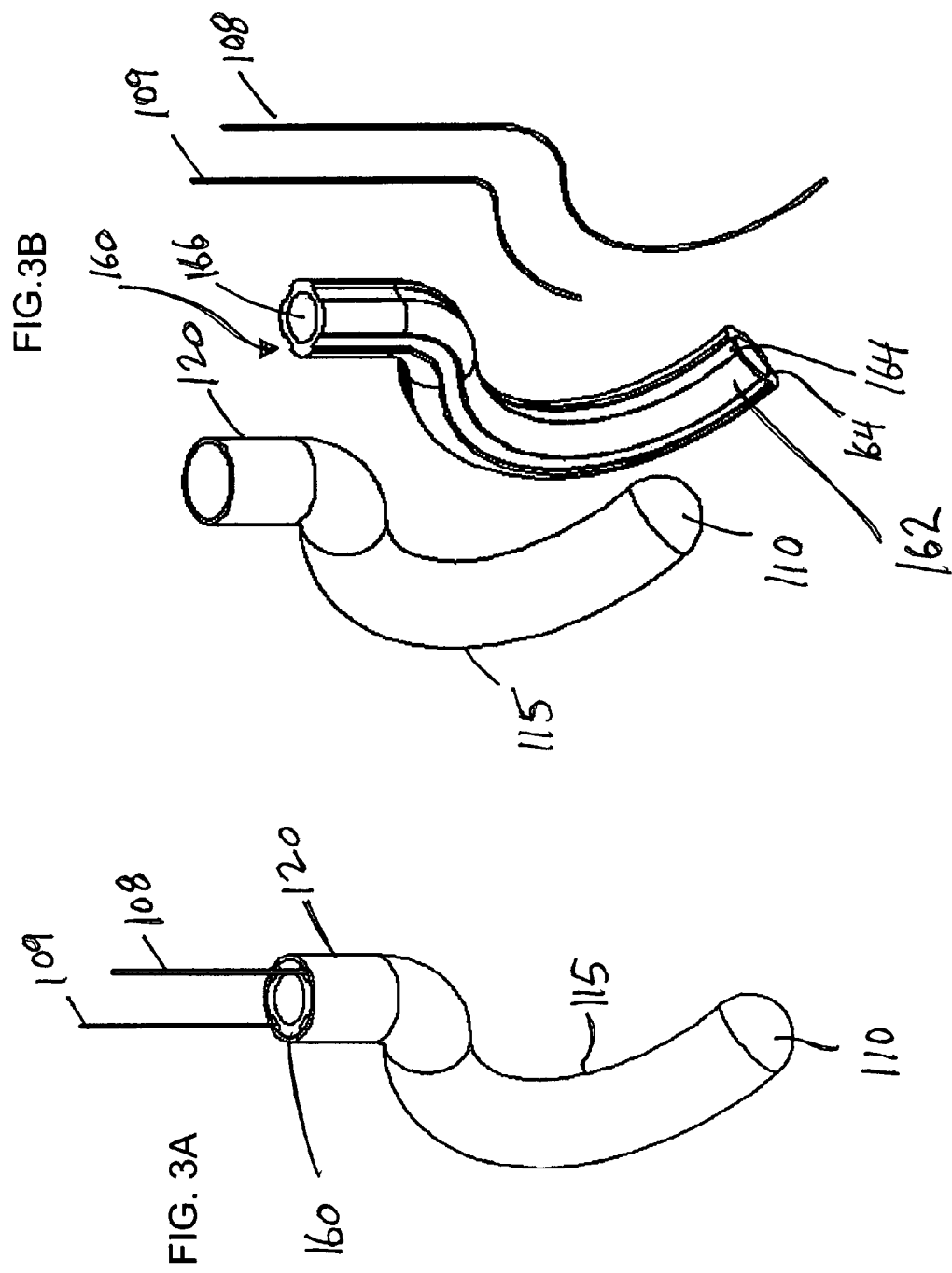

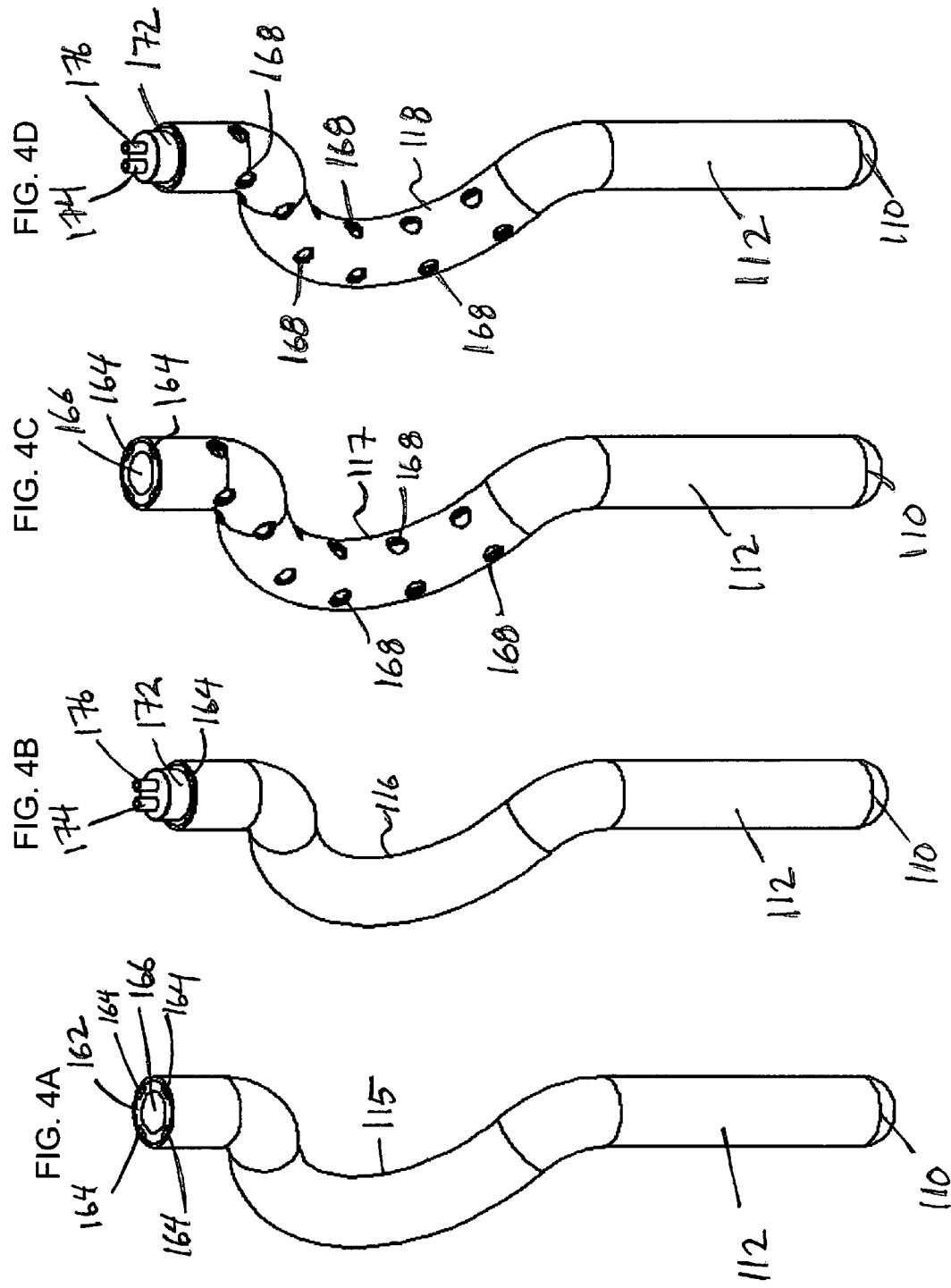

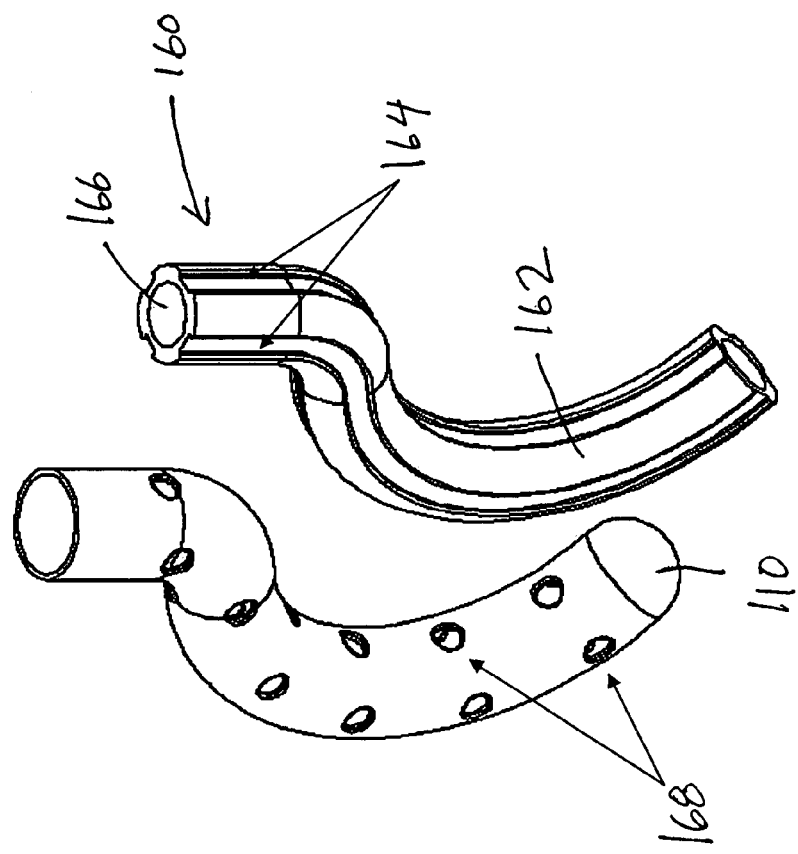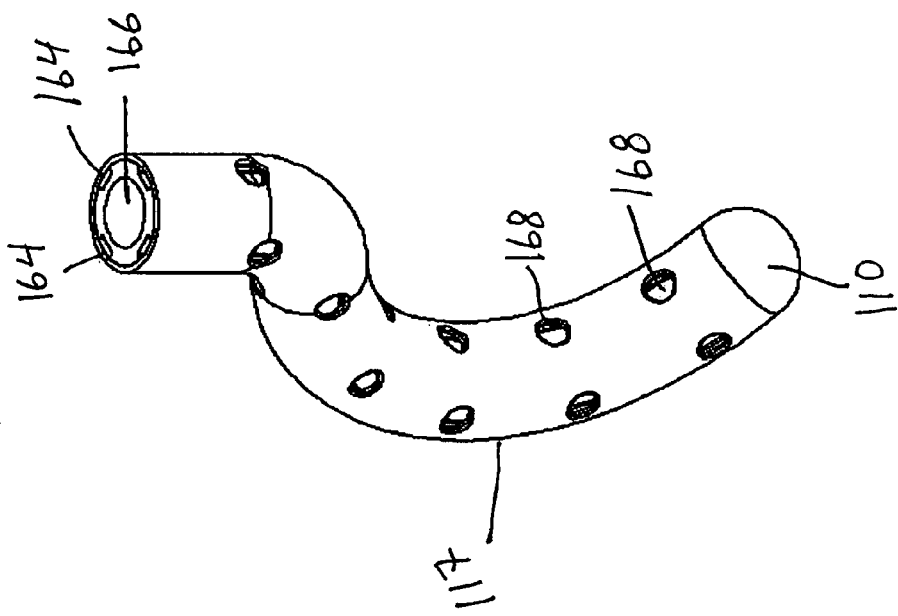

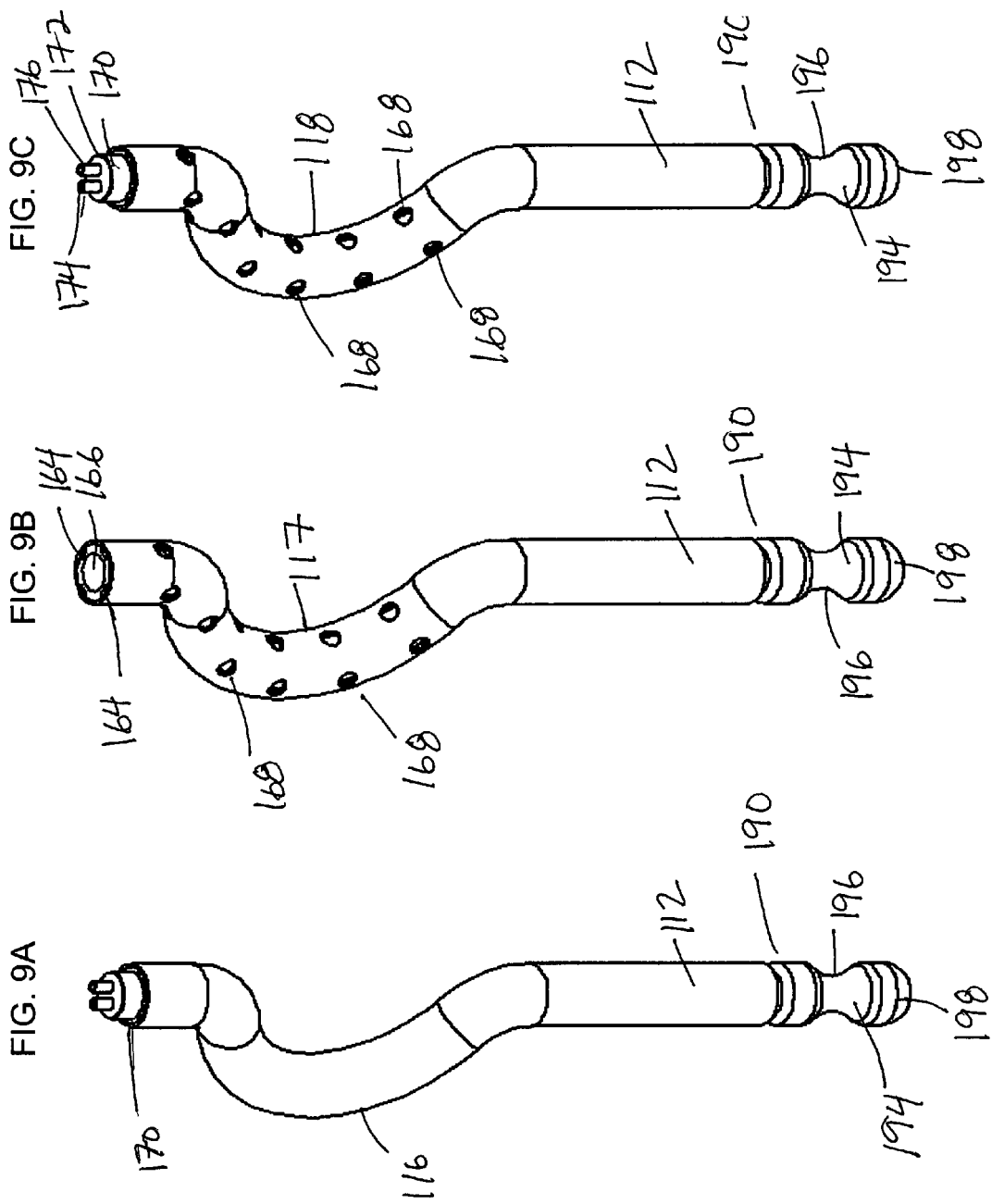

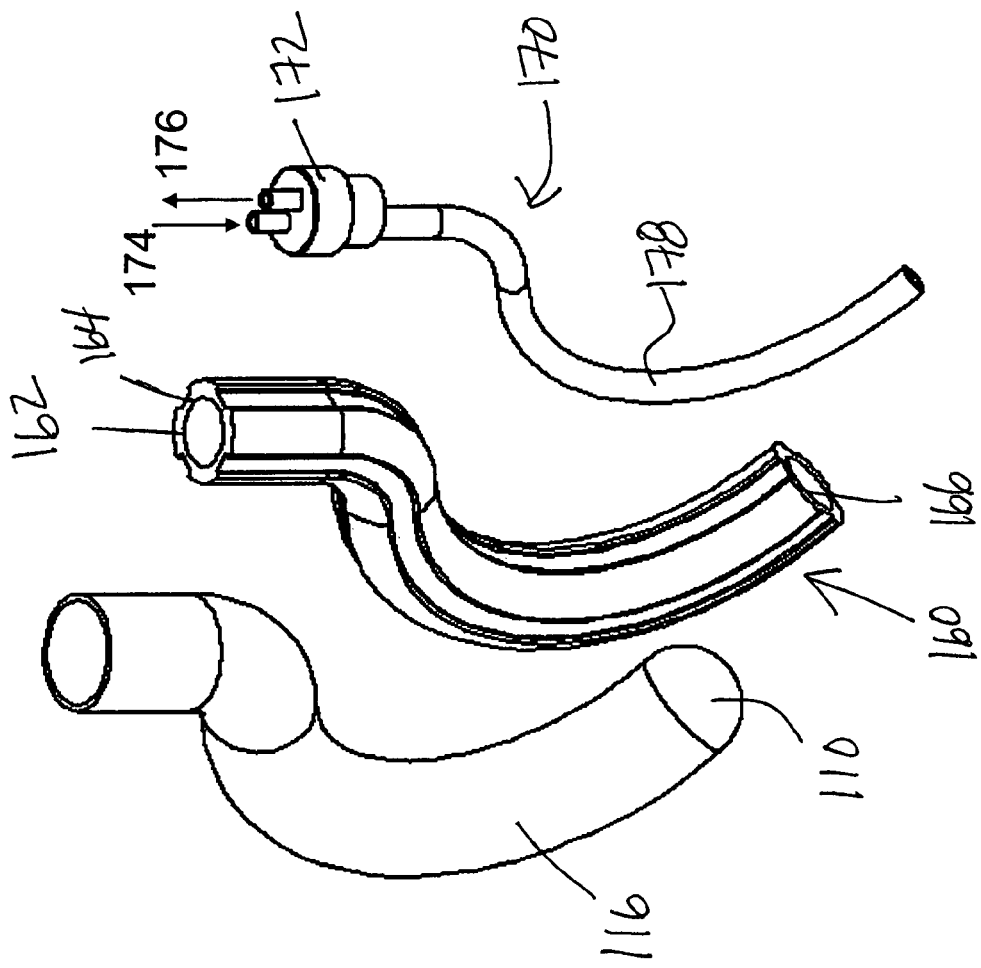
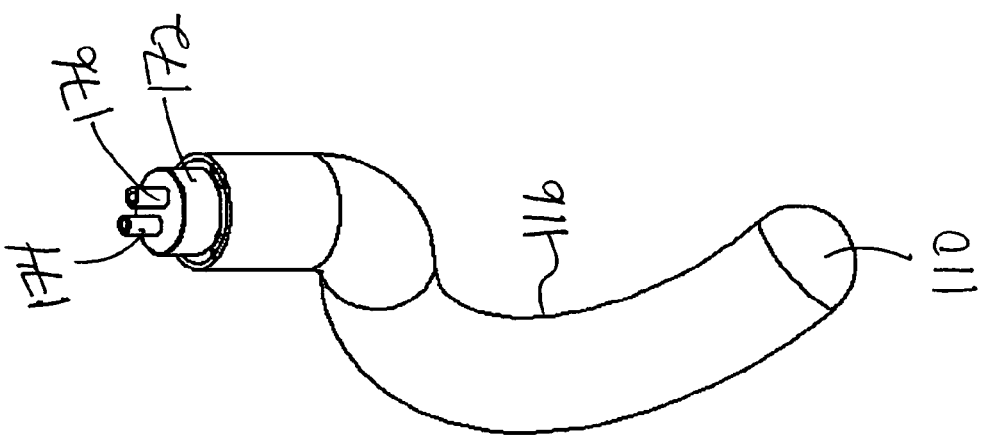
FIG. 12B
FIG. 12A

METHOD AND APPARATUS TO PREVENT ESOPHAGEAL DAMAGE

CROSS REFERENCE TO RELATED APPLICATIONS

This application claims the benefit under 35 U.S.C. 119 of U.S. Provisional Patent Application No. 60/782,827 filed Mar. 17, 2006, and which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference

FIELD OF THE INVENTION

The present application relates to methods and apparatus for protecting the esophagus while a therapy is performed outside of but near the esophagus.

BACKGROUND OF THE INVENTION

Atrial fibrillation is a debilitating medical condition in which the upper chambers of the heart beat in a discoordinated fashion. This can lead to palpitations, breathlessness, fatigue, and stroke. A treatment method that has rapidly gained acceptance as the primary procedure to cure atrial fibrillation is radiofrequency (RF) catheter ablation of the regions in the heart that cause the arrhythmia. Due to the close proximity of the heart and esophagus, RF catheter ablation can lead to life threatening damage to the esophagus since RF energy delivered to the heart can also affect the nearby esophageal tissue. The closer tissue is to a heat source, like an RF therapy site, the more heat is delivered to the tissue since heat flux rate varies as the reciprocal of the square of the radial difference between the tissue and the heat source. Thus, the closeness of the esophagus to the heart causes it to receive a significant amount of heat from adjacent heat therapy sites. In its worst case, esophageal damage can lead to the formation of a connection between the heart and the esophagus, an atrio-esophageal fistula. Approximately 50% of patients suffering this complication die. With an estimated occurrence of up to 1% and nearly 150,000 expected RF ablations by 2010, esophageal damage represents a major threat to patient welfare and a significant burden on the healthcare system. Currently, there is no effective method to directly avoid this dreaded complication during atrial fibrillation ablation procedures without potentially affecting the efficacy of the procedure.

According to the 2002 Health Research International atrial fibrillation marketing report, the incidence of atrio-esophageal fistula formation is estimated to be between 0.5 and 1 percent. However, it is suspected that this number is greatly underreported. Doll and colleagues provide some evidence that the incidence is indeed higher; they reported 4 cases in a series of 129 patients (3.1%) receiving intraoperative RF ablation. Even given the low occurrence, atrio-esophageal fistula formation is a terrible complication with a very high mortality rate (50% mortality rate in reported occurrences). Other events associated with esophageal perforation include air embolism and stroke, endocarditis, mediastinitis, and severe gastrointestinal bleeding. Further morbidity results as patients often develop permanent neurological deficits from air emboli or develop sepsis from endocarditis. Additionally, even if outright fistula formation does not occur, damage to the vagus plexus surrounding the esophagus may give rise to pyloric spasm and gastric hypomobility. Since there have been no detailed studies that have consistently screened patients for esophageal injury after atrial fibrillation ablation, it is difficult to correctly estimate the actual number of patients who suffer non life-threatening esophageal damage during and after ablation. It is believed that esophageal damage during ablation is a severely under-reported phenomenon.

Esophageal damage is a devastating complication of atrial fibrillation ablation. There is no standard approach to prevent this complication. When ablating parts of the heart that are in the vicinity of the esophagus, physicians typically ablate tissue with great care, and often reduce the temperature or power of RF ablation. However, a recent study by Cummings J, Schweiket R, Saliba W, et al: in Circulation 112, 1524 (2005), suggests that there is little or no correlation between RF ablation power and esophageal temperature. Further, a low ablation/RF electrode temperature is likely to result in less effective lesions and therefore, a lower likelihood that the ablation procedure will be successful in the long-run. Moreover, the possibility of damaging the esophagus leads to increased operator anxiety; procedure time also increases due to the extreme care that needs to be taken when ablating in the posterior left atrium (LA) of the heart. Other modifications to the ablation procedure, such as moving posterior wall lesion locations or avoiding posterior lesions altogether, have been suggested, but again raise the possibility of degrading the efficacy of ablation. Further, the anatomic variability of the esophagus makes avoidance of lesions along its course difficult and complications persist.

In view of these shortcomings and challenges, there remains a need for an esophageal protection device for prevention of esophageal damage during therapy to maintain therapy efficacy while therapy is applied to a treatment site outside of but near the esophagus.

SUMMARY OF THE INVENTION

In one aspect, embodiments of the present invention provide an apparatus for moving the esophagus having an elongate body having a distal tip, a controlled curvature section, and a flexible section; and a handle coupled to the flexible section having means for adjusting the curvature of the controlled curvature section. Additionally, the length of the controlled curvature section is less than the length of the thoracic portion of the esophagus. In one aspect, while the apparatus used to bend the esophagus, the distal tip and the controlled curvature section are disposed entirely within the esophagus. In another aspect, while the apparatus used to bend the esophagus, the majority of the flexible section is within the esophagus. In another aspect, the distal tip is flexible. In another aspect, the distal tip further comprises a telescoping member. In another aspect, the distal tip further comprises a bulb adapted to engage with the esophagus. In another aspect, the bulb has a stowed condition for movement to through the esophagus and a deployed condition for engagement with the esophageal sphincter. In another aspect, the distal tip further comprises a bulb having a stowed condition for movement to through the esophagus and a deployed condition for engagement with the esophageal sphincter. In another aspect, the handle comprises an indication of the direction of curvature of the controlled curvature section. In another aspect, any of the tip, the controlled curvature section or the flexible section includes a radio opaque marker or are formed entirely or in part from a radio opaque material. In another aspect, a plurality of apertures are formed in the wall of the controlled curvature section. In another aspect, there is a vacuum source coupled to or in communication with the plurality of apertures formed in the wall of the controlled curvature section. In another aspect, the interior of the controlled curvature section is in communication with a cooling source. In another aspect, the handle comprises a mechanism to adjust the curvature of the controlled curvature section. In another aspect, the mechanism to adjust the curvature of the controlled curvature section is a trigger. In another aspect, the mechanism to adjust the curvature of the controlled curvature section is a knob. In yet another aspect, the mechanism to adjust the curvature of the controlled curvature section further comprises a mechanism to selectively lock the curvature of the controlled curvature section. In another aspect, the elongate body is sized and adapted to enter the esophagus through the nasal passage. In another aspect, the elongate body is sized and adapted to enter the esophagus through the mouth. In another aspect, a temperature sensor on the elongate body is used to measure the temperature of the esophagus. In one aspect, the temperature sensor is in the sidewall of the controlled curvature section and provides a temperature indication on the handle.

In another alternative embodiment, there is provided a method of adjusting the curvature of the esophagus during a therapeutic procedure in a treatment area outside of the esophagus by: positioning within the esophagus an elongate body having a distal tip, a controlled curvature section, and a flexible section wherein, the length of the controlled curvature section is less than the length of the thoracic portion of the esophagus; and adjusting the curvature of the controlled curvature section to increase the distance between the esophagus and a treatment area outside of the esophagus. In another aspect, there is a step of engaging the interior wall of the esophagus with the outer wall of the controlled curvature section. In another aspect, there is the step of cooling the interior wall of the esophagus with the controlled curvature section. In another aspect, there is the step of anchoring the distal tip within the esophagus. In another aspect, anchoring the distal tip within the esophagus comprising positioning a bulb into the esophageal sphincter. In another aspect, positioning a bulb into the esophageal sphincter comprises deploying the bulb to engage with the esophageal sphincter. In another aspect, there is the step of increasing the distance between the esophagus and an ablation site. In another aspect there is the step of creating an anterior posterior curvature within the esophagus. In another aspect, there is the step of creating an lateral medial curvature within the esophagus. In another aspect, there is the step of controlling the curvature of the controlled curvature section by adjusting a mechanism on a handle attached to the elongate body. In another aspect, there is the step of using a locking device to lock the position of the controlled curvature section. In another aspect, there is the step of controlling the curvature of the controlled curvature section by adjusting a bendable element disposed within the controlled curvature section.

In yet another embodiment, there is an apparatus for moving the esophagus having a flexible elongate body having a distal tip, a controlled curvature section, and a proximal section; and a bendable element within the controlled curvature section that, when bent, moves and holds the controlled curvature section into a corresponding bent shape. In one aspect, the bendable element is a wire. In another aspect, the bendable element extends along the length of the proximal section.

In another aspect, the length of the controlled curvature section is less than the length of the thoracic portion of the esophagus.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In the drawings:

FIG. 1A is an isometric view of an apparatus to move the esophagus having a handle with a trigger to control the curvature of the controllable curvature section;

FIG. 2A is an isometric view of the apparatus to move the esophagus in FIG. 1A illustrating the trigger actuated to bend the controllable curvature section of the apparatus;

FIGS. 2C, 2D and 2E are side views of an apparatus to move the esophagus having controlled curvature sections of different length to bend the esophagus into different curves;

FIG. 2H is an isometric view of an apparatus to move the esophagus having a slide to control the curvature of the controllable curvature section and a friction lock to hold the curvature of the controllable curvature section;

FIG. 2I is an isometric view of the apparatus to move the esophagus in FIG. 2H illustrating the slide actuated to bend and the friction lock to hold the controllable curvature section;

FIG. 3A is an isometric view of an controlled curvature section exposed to show the internal section components;

FIG. 3B is an exploded view of the controlled curvature section in FIG. 3A showing the internal section components;

FIG. 4A is an isometric view of an controlled curvature section having an extended distal section between the distal tip and the controlled curvature section;

FIG. 4B is an isometric view of the controlled curvature section in FIG. 4A showing additional internal section components to add cooling capability to the controlled curvature section;

FIG. 4C is an isometric view of the controlled curvature section in FIG. 4A showing additional section variations to add suction capability to the controlled curvature section;

FIG. 4D is an isometric view of the controlled curvature section in FIG. 4A showing additional internal section components to add both cooling and suction capability to the controlled curvature section;

FIG. 6A is an isometric view of an controlled curvature section exposed to show the internal section components to add suction capabilities;

FIG. 6B is an exploded view of the controlled curvature section in FIG. 6A showing the internal section components to add suction capabilities;

FIG. 9A is an isometric view of the apparatus to move the esophagus in FIG. 8A showing additional internal section components to add cooling capability to the controlled curvature section;

FIG. 9B is an isometric view of the apparatus to move the esophagus in FIG. 8A showing additional section variations to add suction capability to the controlled curvature section;

FIG. 9C is an isometric view of the apparatus to move the esophagus in FIG. 8A showing additional internal section components to add both cooling and suction capability to the controlled curvature section;

FIG. 12A is an isometric view of a controlled curvature section exposed to show the internal section components to add cooling capabilities;

FIG. 12B is an exploded view of the controlled curvature section in FIG. 12A showing the internal section components;

DETAILED DESCRIPTION OF THE INVENTION

It is believed that an esophageal protection device according to one or more embodiments of the present invention is capable of safely reducing the likelihood of all or some of the complications of esophageal damage, atrio-esophageal fistula, and esophageal perforation by allowing a user, such as a physician or other medical care practitioner, to manually shift the esophagus away from a therapy site in order to reduce the likelihood of esophagus damage.

Figure 1B:
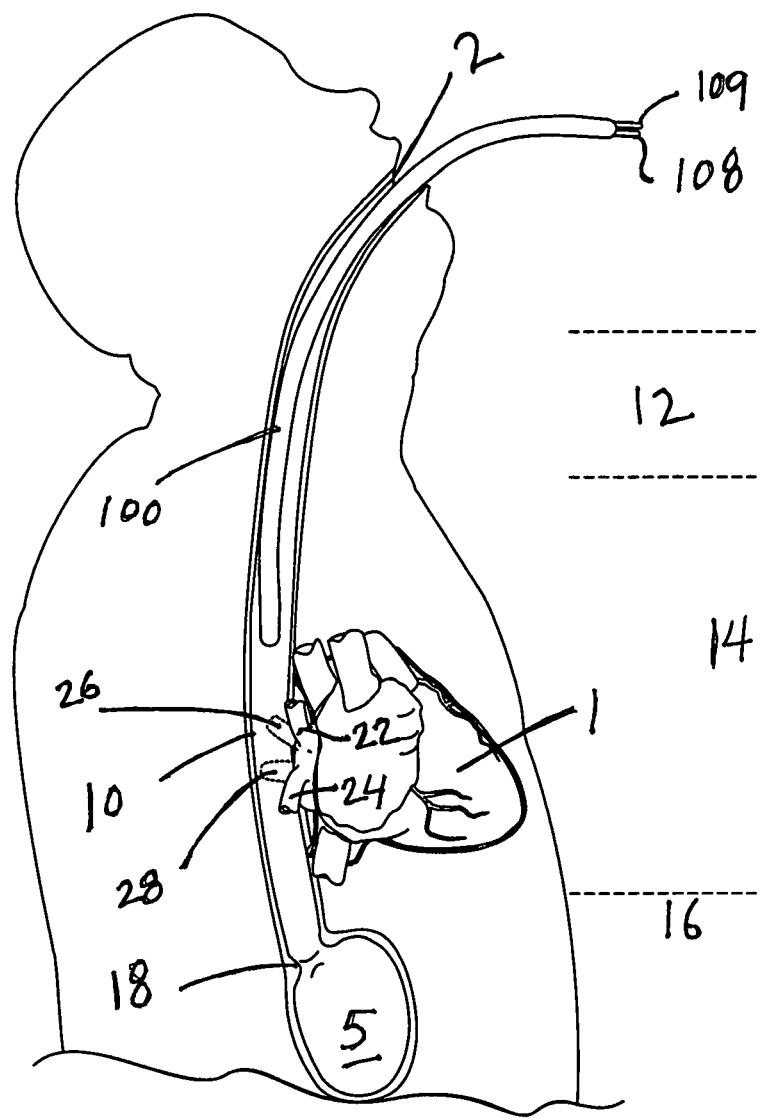
FIG. 1B is a section view of the thoracic portion of the body with the device of FIG. 1A in place in the esophagus.

FIG. 1A is an isometric view of an apparatus 100 to move the esophagus according to one embodiment of the invention. The apparatus 100 has an elongate body 105 having a distal tip 110, a controlled curvature section 115, and a flexible section 120. A handle 125 is coupled to the flexible section 120 having means for adjusting the curvature of the controlled curvature section 115. In the illustrated embodiment, handle 130 has a trigger 130 to control the curvature of the controllable curvature section 115 using a conventional ratchet mechanism (not shown) contained within the handle 125. The trigger 130 and ratchet mechanism are connected to one or more tendons 108 (see FIG. 1B) that are in turn connected to the controlled curvature section 115. The tendons may be any suitable wire. One exemplary tendon could also be stainless steel cable. The material used to form the tendon or tensioning element may also be coated with Teflon or other material to increase tendon lubricity. In these embodiments, tensioning member movement causes changes in the curvature of the controlled curvature section 115. One example of a tensioning element is a tendon such as described below. Adjusting the tensioning element results in bending of the controlled curvature section. Other components of the elongate body are not bent.

The controllable curvature section 115 could be made from a highly flexible material such as reinforces poly-ethylene and the like. Additionally or alternatively, all or selected portions of the proximal and/or distal portions of the controllable curvature section 115 may be coated with a heat treat material and thereafter subjected to heat treatment to selectively create regions of different stiffness to aid in bending the section. Similarly, the section 115 could also be heat treated such that it forms a predefined shape when placed under tension by the tendons. One illustrative material for performing heat treatment is Teflon. Alternatively, the controllable section 115 may be formed from an extrusion of PEBAX with internal reinforcements such as polyimide and the like. The other components of the elongate body are made from flexible materials to allow for introduction into the esophagus but these other portions of the body 105 are not configured or adapted for controllable movement. As such, rather than an elongate body 105 of homogeneous construction, there are embodiments of the invention where the portions of the elongate body 105 proximal and/or distal to the controllable curvature section 115 have a different construction than the controllable section 115. The controllable section 115 is a section of different construction and purpose that the distal tip 110 and the flexible section 120.

FIG. 1B is a sagittal section view of the thoracic portion of the body with the device 100 of FIG. 1A in place in the esophagus 10. As shown in this view, the apparatus 100 has been adapted and configured to enter the esophagus 10 through the mouth 2. In one embodiment, the apparatus 100 includes an elongate body 105 attached to a handle 125. The elongate body 105 is sufficiently flexible to enter the esophagus through the mouth or the nasal passage. In the illustrated embodiment, the elongate body 105 includes a distal tip 110, a controlled curvature section 115 and a flexible section 120. The elongate body 105 could be formed from elastomeric tubing suited to medical applications.

The elongate body 105 is adapted and configured to deflect a portion of the esophagus, in addition to the other functionalities detailed herein. The esophagus 10 is a muscular canal, about 23 to 25 cm. long, extending from the pharynx to the stomach 5. The esophagus 10 begins in the neck at the lower border of the cricoid cartilage, opposite the sixth cervical vertebra, descends along the front of the vertebral column, through the superior and posterior mediastina, passes through the diaphragm, and, entering the abdomen, ends with the esophageal sphincter 18 at the cardiac orifice of the stomach 5, opposite the eleventh thoracic vertebra.

It is believed that the close anatomical relationship between the LA and the esophagus leads to thermal injury to the esophagus during ablation along the posterior wall of the LA and can result in the formation of a fistula between the atria and the esophagus. The proximity of the esophagus to the posterior LA is clearly evident in FIG. 1B. The esophagus has three portions: the cervical portion 12, the thoracic portion 14 and the abdominal portion 16. Anatomical descriptions of each of the portions follow.

The cervical portion 12 of the esophagus 10 is in relation, in front, with the trachea; and at the lower part of the neck, where it projects to the left side, with the thyroid gland; behind, it rests upon the vertebral column and Longus colli muscles; on either side it is in relation with the common carotid artery, and parts of the lobes of the thyroid gland; the recurrent nerves ascend between it and the trachea; to its left side is the thoracic duct.

The thoracic portion 14 of the esophagus 10 is at first situated in the superior mediastinum between the trachea and the vertebral column, a little to the left of the median line. It then passes behind and to the right of the aortic arch, and descends in the posterior mediastinum along the right side of the descending aorta, then runs in front and a little to the left of the aorta, and enters the abdomen through the diaphragm at the level of the tenth thoracic vertebra. Just before it perforates the diaphragm it presents a distinct dilatation. It is in relation, in front, with the trachea, the left bronchus, the pericardium, and the diaphragm; behind, it rests upon the vertebral column, the Longus colli muscles, the right aortic intercostal arteries, the thoracic duct, and the hemiazygos veins; and below, near the diaphragm, upon the front of the aorta. On its left side, in the superior mediastinum, are the terminal part of the aortic arch, the left subclavian artery, the thoracic duct, and left pleura, while running upward in the angle between it and the trachea is the left recurrent nerve; below, it is in relation with the descending thoracic aorta. On its right side are the right pleura, and the azygos vein which it overlaps. Below the roots of the lungs the vagi descend in close contact with it, the right nerve passing down behind, and the left nerve in front of it; the two nerves uniting to form a plexus around the tube. In the lower part of the posterior mediastinum the thoracic duct lies to the right side of the esophagus; higher up, it is placed behind it, and, crossing about the level of the fourth thoracic vertebra, is continued upward on its left side.

The abdominal portion 16 of the esophagus 10 lies in the esophageal groove on the posterior surface of the left lobe of the liver. It measures about 1.25 cm. in length, and only its front and left aspects are covered by peritoneum. This portion of the esophagus is somewhat conical with its base applied to the upper orifice of the stomach, and is known as the antrum cardiacum.

Although there is significant anatomic variability across individuals, in general, the esophagus and LA lie in close proximity in the posterior mediastinum of the thorax. The specific anatomic region most relevant to fistula formation is the aspect of the posterior mediastinum bordered posteriorly by the esophagus and anteriorly by the pericardium. The esophagus and the LA typically lie in contact in a region that extends from the middle portion of the posterior LA to the lower border of inferior PVs. Research has shown that the longitudinal length of the contact region between the LA and esophagus is about 42±7 mm. The contact region lies entirely within the thoracic portion of the esophagus. Due to displacement of the aortic arch, the extent of longitudinal contact between the esophagus and LA is highly variable. The transverse width of the esophagus along the contact region is typically 13.5±5 mm. The mean thickness of the esophageal wall adjacent to the LA is approximately 2.5±1 mm. Anteriorly, the posterior wall of the LA has a variable thickness depending on the specific location with a typical range of 1.7 to 5 mm, although some individuals may have wall thickness of less than 1 mm. The beating of the heart, respiration, and peristaltic movement of the esophagus contribute to intermittent direct contact between the esophagus and the LA. The esophagus is a mobile structure and the specific points of contact with the LA may vary as the esophagus shifts. Transverse esophageal mobility has been shown to have an average range of 0.3 to 3.8 cm and anterior-posterior separation distance between the esophagus and LA averages 5 mm. Finally, an anatomic space exists between the esophagus and LA of heterogeneous composition. The space can contain lymph nodes, branches of the vagus nerve, fibrofatty deposits, and significant vasculature.

FIG. 2A is an isometric view of the apparatus to move the esophagus in FIG. 1A illustrating the trigger actuated to bend the controllable curvature section of the apparatus. The handle 125 includes an indication of the direction of curvature of the controlled curvature section. In this embodiment, the flat upper portion of the handle is in line with the bend induced in section 115. In this way, a user may know the direction of bending produced by the section 115. If the bend resulting from adjusting the curvature of the section produces a curve in a different location relative to the handle, then a different portion of the handle may be marked for indication orientation to the bend of section 115.

Figure 2B:
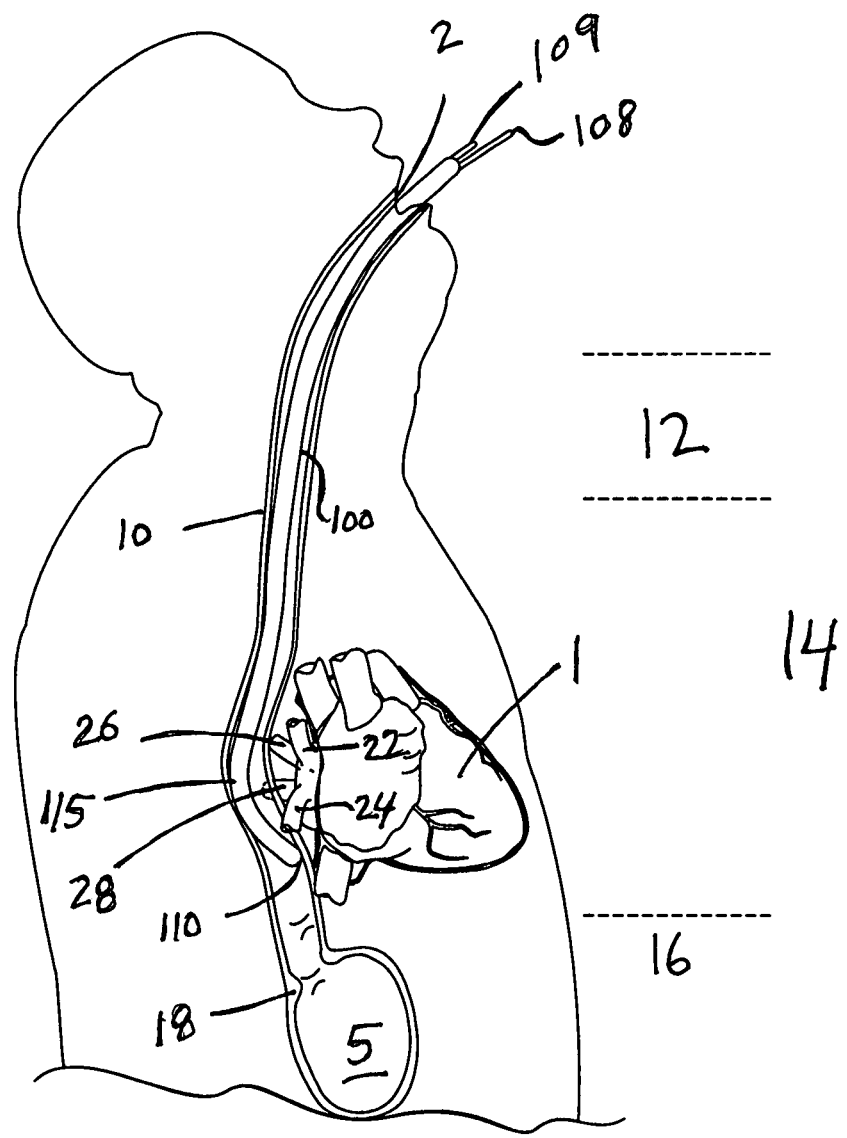
FIG. 2B is a section view of the thoracic portion of the body with the device of FIG. 2A in place in and moving the esophagus.

FIG. 2B is a sagittal section view of the thoracic portion of the body with the device 100 of FIG. 2A in place in and moving the esophagus 10. The controlled curvature section 115 is within the thoracic portion near in the vicinity closest to the heart 1. In one embodiment adapted and configured for protecting the esophagus during ablation in the vicinity of the pulmonary veins 22, 24, 26, and 28 the length of the controlled curvature section 115 is less than the length of the thoracic portion 14 of the esophagus 10. In one exemplary embodiment, the length of the controlled curvature section 115 is in the range of 10 to 100 mm. In another embodiment, the length of the section 115 is in the range of 30-50 mm. In another embodiment, the length of the controlled curvature section 115 is section within the range from one quarter of the length of the longitudinal overlap between the esophagus and the LA to twice the length of the longitudinal overlap between the esophagus and the LA.

The controlled curvature section 115 is used to move the esophagus 10 away from the area of therapy, here, in the vicinity of the pulmonary veins 22, 24, 26, and 28. The illustrated embodiment shows how adjusting the curvature of the controllable curvature section 115 increases the distance between the esophagus 10 and a treatment area outside of the esophagus.

FIG. 2B also illustrates how adjusting the curvature of the controllable curvature section 115 creates an anterior posterior curvature within the esophagus 10. Additionally, the curvature illustrated may also produce a lateral medial curvature within the esophagus 10. The amount of esophageal curvature is determined by a number of factors. One factor is the position of the controllable curvature section within the esophagus. Another factor is the degree of curvature adjustment applied to the controlled curvature section 115 by the means for adjusting the curvature. Another factor is the length of the controllable section 115 available to impart bend. In all embodiments of the invention, the amount of curvature imparted to the esophagus is both atraumatic to the esophagus and reversible meaning that when the bend is removed the esophagus is not permanently deformed into a bent condition.

FIGS. 2C, 2D and 2E are side views of an apparatus to move the esophagus having controlled curvature sections of different length to bend the esophagus into different curves. FIG. 2C illustrates a controlled curvature section 115A having a length $l_1$. The length $l_1$ can be adjusted into a variety of curves including the illustrated curvature having a radius $r_1$. FIG. 2D illustrates a controlled curvature section 115B having a length $l_2$ shorter than the length $l_1$. The length $l_2$ can be adjusted into a variety of curves including the illustrated curvature having a radius $r_2$. FIG. 2E illustrates a controlled curvature section 115C having a length $l_3$ longer than the length $l_1$. The length $l_3$ can be adjusted into a variety of curves including the illustrated curve having a radius $r_3$. As such, for a given controlled curvature section 115 length, the means for adjusting the curvature of the controlled curvature section can adjust the bend, radius or curvature of the controllable curvature section within the curvature range available for the given length of the controllable section 115. In one embodiment, the radius and length of the section 115 is selected to produce movement of the esophagus within the range of 0.3 to 4 cm. In yet another embodiment, the radius and length of the section 115 is selected that will produce movement of the thoracic esophagus within the range of 0.3 to 4 cm. In yet another embodiment, the radius and length of the section 115 is selected to produce movement of the esophagus adjacent the LA within the range of 0.3 to 4 cm. In another embodiment, the length of the section 115 and the radius is selected to move the entire overlap section between the esophagus and the LA. In one specific embodiment, the bend radius of the controlled curvature section is selected within the range of 2.5 mm to 625 mm.

Figures 2F, 2G:
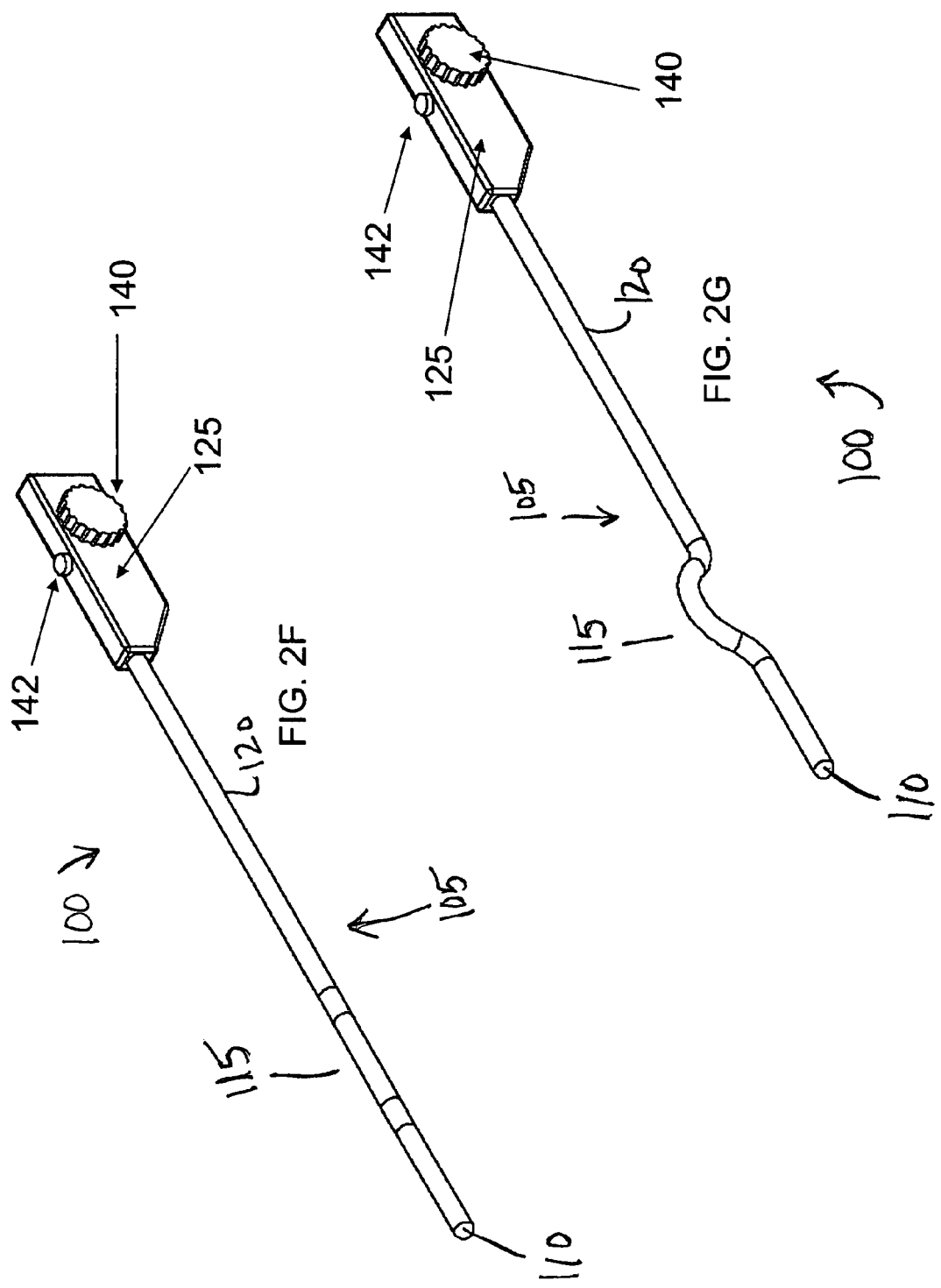
FIG. 2F is an isometric view of an apparatus to move the esophagus having a handle with a knob to control the curvature of the controllable curvature section and a ratchet release button to remove the curvature of the controllable curvature section.
FIG. 2G is an isometric view of the apparatus to move the esophagus in FIG. 2F illustrating the knob actuated to bend the controllable curvature section of the apparatus.

In addition to the trigger 130 illustrated in FIGS. 1A and 2A, other means for adjusting and locking the curvature of the controlled curvature section 115 are possible. FIG. 2F is an isometric view of an apparatus to move the esophagus having a handle 125 with a knob 140 to control the curvature of the controllable curvature section 115. In this embodiment, the mechanism to adjust the curvature of the controlled curvature section 115 is the conventional ratchet mechanism associated with knob 140. Engagement of the ratchet mechanism is another way of using a locking device to lock the position of the controllable curvature section.

Rotation of knob 140 uses a conventional ratchet mechanism within the handle 125 to pull on one or more tendons attached to the controllable curvature section 115. The ratchet selectively locks the curvature of the controlled curvature section as the knob 140 rotates. The amount of rotation of the knob 140 determines the amount of the adjustment of the controlled curvature section 115. The handle 125 includes a ratchet release button 142 to release the ratchet mechanism thereby allowing the controllable curvature section 115 to return to an unbent condition. FIG. 2G is an isometric view of the apparatus to move the esophagus in FIG. 2F illustrating the knob 140 actuated to bend the controllable curvature section 115 of the apparatus.

FIG. 2H is an isometric view of an apparatus to move the esophagus having a conventional slide mechanism 135 to control the curvature of the controllable curvature section 115. The conventional slide mechanism 135 is another alternative means for adjusting the curvature of the controllable curvature section 115. The tab 138 is connected to one or more tendons connected to the controllable curvature section 115. Movement of the tab 138 proximally within the groove 136 adjusts the curvature of the controllable curvature section 115. A conventional friction lock 150 is provided to fix the tab 138 within the groove 136. Engagement of the friction lock 150 is another way of using a locking device to lock the position of the controllable curvature section. Movement of lever 152 within the slot 154 engages a friction lock to hold the tab 138 in position within groove 136. FIG. 2I is an isometric view of the apparatus to move the esophagus in FIG. 2H illustrating the slide mechanism 135 actuated to bend the controllable curvature section 115. The lever 152 has moved to the proximal most portion of the slot 154. In this position, the friction lock 150 holds the controllable curvature section in the bent condition as shown.

FIG. 3A is an isometric view of a controlled curvature section 115 exposed to show the internal section components. FIG. 3B is an exploded view of the controlled curvature section 115 in FIG. 3A showing the internal section components. The guide body 160 is an elongate body adapted to fit within the controllable curvature section 115. As will be seen in the embodiments that follow, the guide body 160 is adapted into various different configurations to provide added functionality to the controlled curvature section 115. In this embodiment, the guide body 160 may optionally have a hollow central portion 166. The guide body 160 includes grooves 164 on the outer surface of the body 160. Grooves 164 extend along the longitudinal axis of the body 160. Four grooves 164 are shown and more or fewer grooves may be provided depending upon application. In this embodiment the grooves 164 are used to house and secure tendons 108, 109. The grooves 164 are shaped to accommodate the size of tendons used so that the tendons do not protrude above the outer surface of the body 162. Additional groves or extrusions of the guide body 160 may be used to generate, or aid in generation of, specific curvatures of the controlled curvature section 115. The stiffness of the guide body 160 may also be varied along its length to generate, or aid in generation of, specific curvatures of the controlled curvature section 115.

Tendons 108, 109 are of different lengths and extend back through the elongate body 105 to a suitable connection in the handle 125 and the mechanism therein for adjusting the curvature of the controlled curvature section 115. The one or more tendons terminate and attach to the elongate body 105 within the controllable section 115. Tendons do not extend into or attach to the tip 110. The tendons may attach at different points within the section 115 to introduce different degrees of bend into the section. Tendons may be positioned within section 115 to curve and produce a lateral medial bend of the esophagus. Additionally or alternatively, tendons may be positioned within section 115 to curve and produce an anterior posterior bend of the esophagus. It is to be appreciated that section 115 may be configured to bend through the use of only one tendon or using three or more tendons. Alternatively, instead of using the guide body 160, the one or more tendons may be attached directly to the interior wall of section 115, if the section 115 is hollow or within section 115, if the section 115 is solid.

Figure 3E:
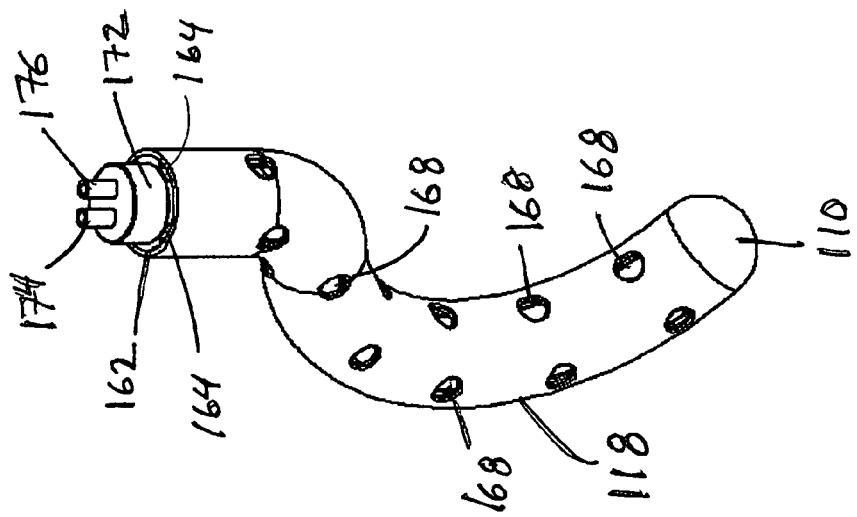
FIG. 3E is an isometric view of the controlled curvature section in FIG. 3A showing additional internal section components to add both cooling and suction capability to the controlled curvature section.

As mentioned previously, the body 162 may be modified to provide functionality in addition to bending the controllable section 115. For clarity, the one or more tendons used to bend section 115 are not shown. FIG. 3C is an isometric view of the controlled curvature section 115 in FIG. 3A showing additional internal section components to add cooling capability to form the cooled, controlled curvature section 116. In this embodiment, a cooling insert 170 is inserted into the central portion 166. Additional details and views of the cooling functionality are described below with regard to FIGS. 12A, 12B and 12C.

Figure 3D:
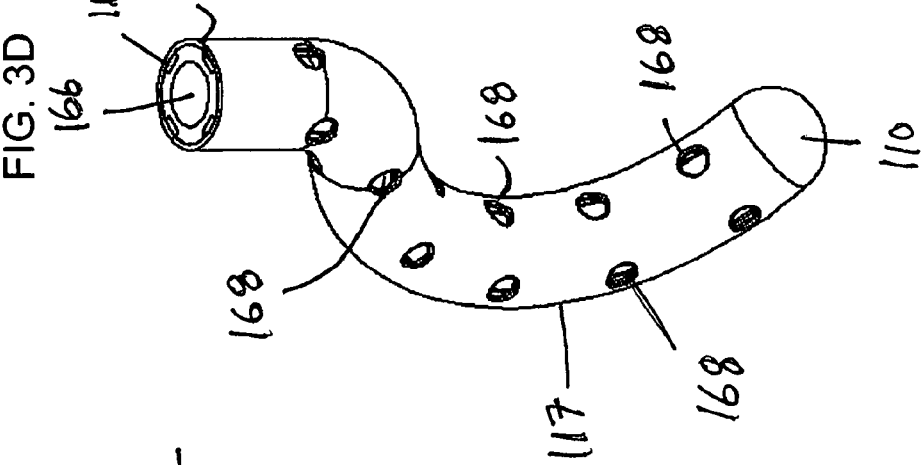
FIG. 3D is an isometric view of the controlled curvature section in FIG. 3A showing additional section variations to add suction capability to the controlled curvature section.
Figure 3C:
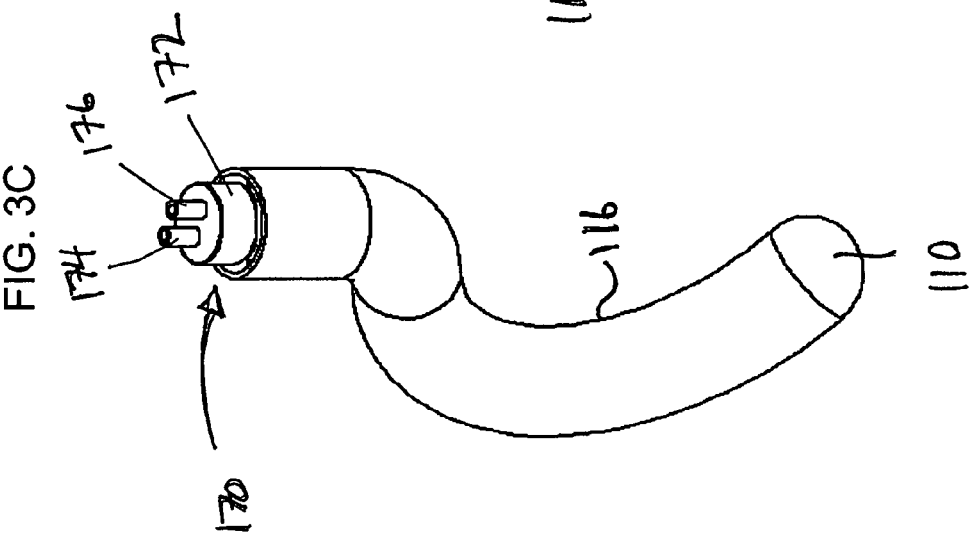
FIG. 3C is an isometric view of the controlled curvature section in FIG. 3A showing additional internal section components to add cooling capability to the controlled curvature section.

FIG. 3D is an isometric view of the controlled curvature section 115 in FIG. 3A showing additional section variations to add suction capability and form a suction capable, controlled curvature section 117. In this embodiment, grooves 164 are aligned with apertures 168 formed in the sidewall of the section 115. The grooves 164 are also in communication with a conventional vacuum source suited to medical application. Sufficient vacuum is applied to section 116 to hold the esophagus against the section during movement. Additional details and views of the suction functionality are described below with regard to FIGS. 6A, 6B and 6C.

FIG. 3E is an isometric view of the controlled curvature section in FIG. 3A showing additional internal section components to add both cooling and suction capability to form the controlled curvature section 118.

In alternative embodiments of the apparatus to move the esophagus, the controllable section 115 may be moved proximally away from the distal tip 110 through the addition of a flexible but not controllable section 112. The section 112 may be of any suitable length to aid the bendable section 115 in moving the esophagus 10. When used in the esophagus, the section 112 could lie completely within the thoracic portion 14, the abdominal portion 16 or within both portions. While not intending to be bound by theory, it is believed that in use, the section 112 acts as the distal support portion in cooperation with a proximal support portion provided by the flexible section 120 adjacent the controllable section 115. In embodiments having the section 112, the section 112 and portion of the section 120 act as the base for ensuring that the section 115 remains in apposition to the esophagus during bending or movement.

FIG. 4A is an isometric view of a controlled curvature section as shown in FIG. 3A having an extended distal section 112 between the distal tip 110 and the controlled curvature section 115. FIG. 4B is an isometric view of the controlled curvature section in FIG. 4A modified as in FIG. 3C showing additional internal section components to add cooling capability to provide the controlled curvature section 116. FIG. 4C is an isometric view of the controlled curvature section in FIG. 4A modified as in FIG. 3D showing additional section variations to add suction capability to the controlled curvature section 117. FIG. 4D is an isometric view of the controlled curvature section in FIG. 4A modified as in FIG. 3E showing additional internal section components to add both cooling and suction capability to provide the controlled curvature section 118.

Figure 5A:
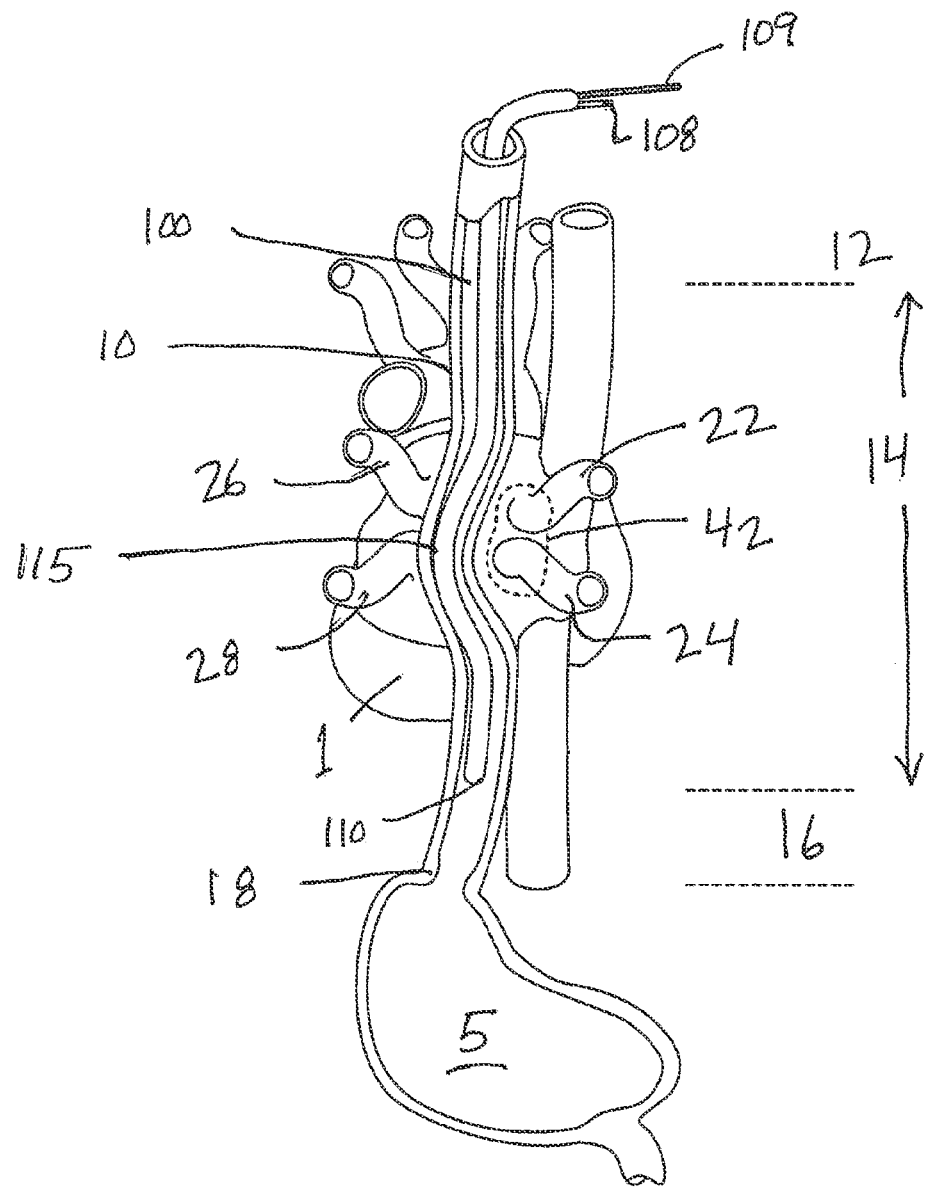
FIG. 5A is a posterior section view of the thoracic portion of the body with the device of FIG. 2A positioned in and moving the esophagus away from a therapy site adjacent the right upper and lower pulmonary veins (PVs)
Figure 5B:
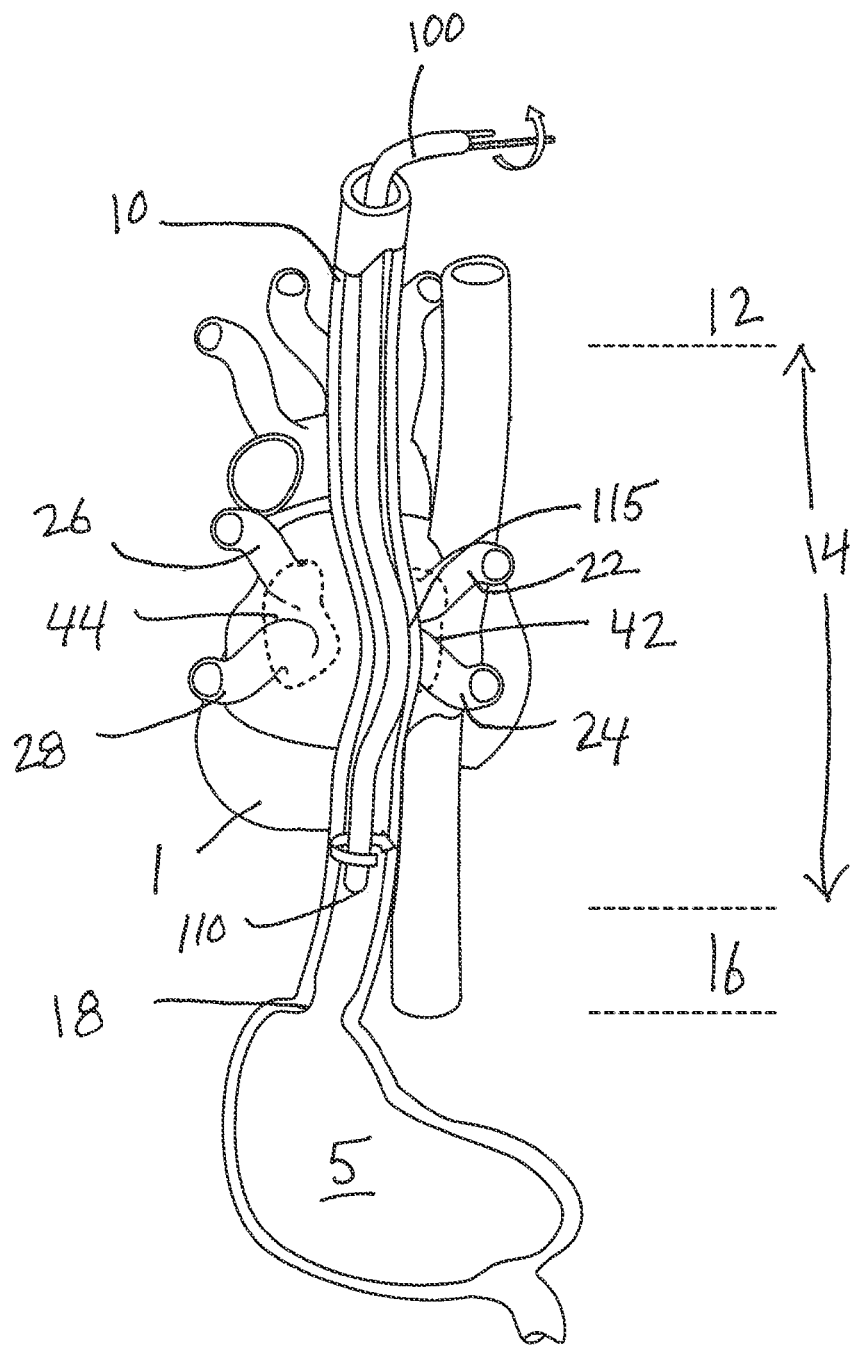
FIG. 5B is a posterior section view of the device of FIG. 2A after rotation of the locked device to move the esophagus away from a therapy site adjacent the left upper and lower PVs.

FIG. 5A is a posterior section view of the thoracic portion of the body with the device of FIG. 2A positioned in and moving the esophagus 10 away from a therapy site 42 indicated by dashed lines. The therapy site 42 is an example of a treatment area outside of the esophagus. The therapy site 42 is adjacent the right upper and lower pulmonary veins 22, 24. As shown in FIG. 5A, adjusting the section 115 increases the distance between the esophagus and a treatment area outside of the esophagus. FIG. 5B is a posterior section view of the device of FIG. 2A after rotation of the locked device to move the esophagus 10 away from a therapy site 44 indicated by the dashed lines. The therapy site 44 is another example of a treatment area outside of the esophagus. The therapy site 44 is adjacent the left upper and lower pulmonary veins 26, 28. Using an indicator on the handle or other landmarks to indicate the orientation of the section 115, the section could be bent, locked and then rotated as shown to move the esophagus 10.

FIG. 6A is an isometric view of a controlled curvature section exposed to show the internal section components to add suction capabilities. The tendons used to bend the section are not shown for clarity. FIG. 6B is an exploded view of the controlled curvature section in FIG. 6A showing the internal section components to add suction capabilities. The body 166 may be hollow or solid. In this embodiment, grooves 164 are aligned with apertures 168 formed in the sidewall of the section 115. The grooves 164 are also in communication with a conventional vacuum source suited to medical application. Sufficient vacuum is applied to section 116 to hold the esophagus against the section during movement. In an alternative embodiment, the central portion 166 is in communication with a vacuum source. Instead of using grooves 164, apertures (not shown) in the sidewall of the body 162 are in communication with apertures 168.

Figure 6C:
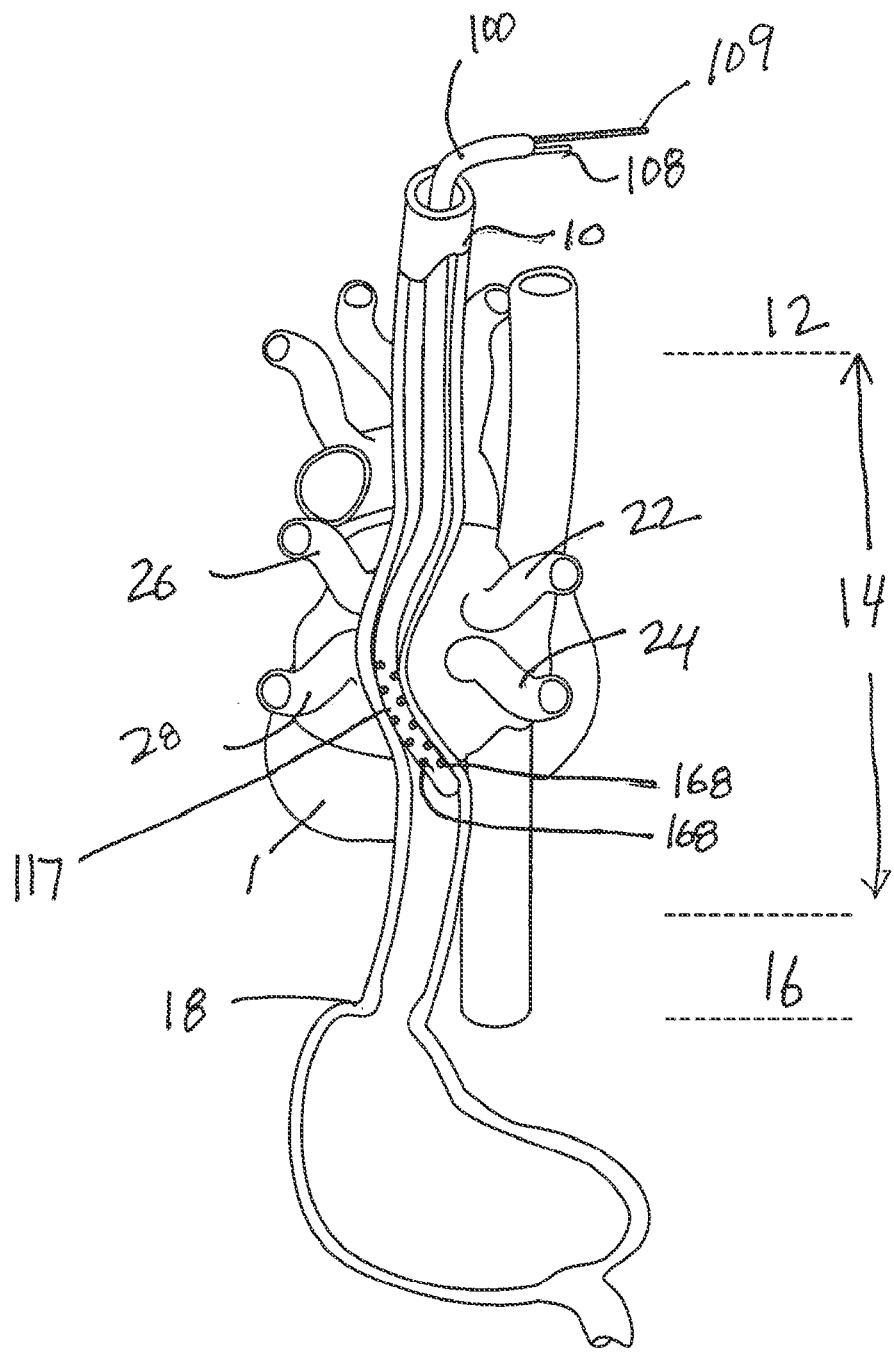
FIG. 6C is a posterior section view of the thoracic portion of the body with the device of FIG. 6A in place in, applying suction to and moving the esophagus.

FIG. 6C is a posterior section view of the thoracic portion of the body with the device of FIG. 6A in place in within the thoracic portion 14 of the esophagus 10. The section 117 is bent to move the esophagus. Suction is being applied to the apertures 168 to pull the esophagus against the section 117. In this way, movement and/or curvature of the esophagus is more certain to directly correspond to the user adjusted curvature of section 117.

Figure 7:
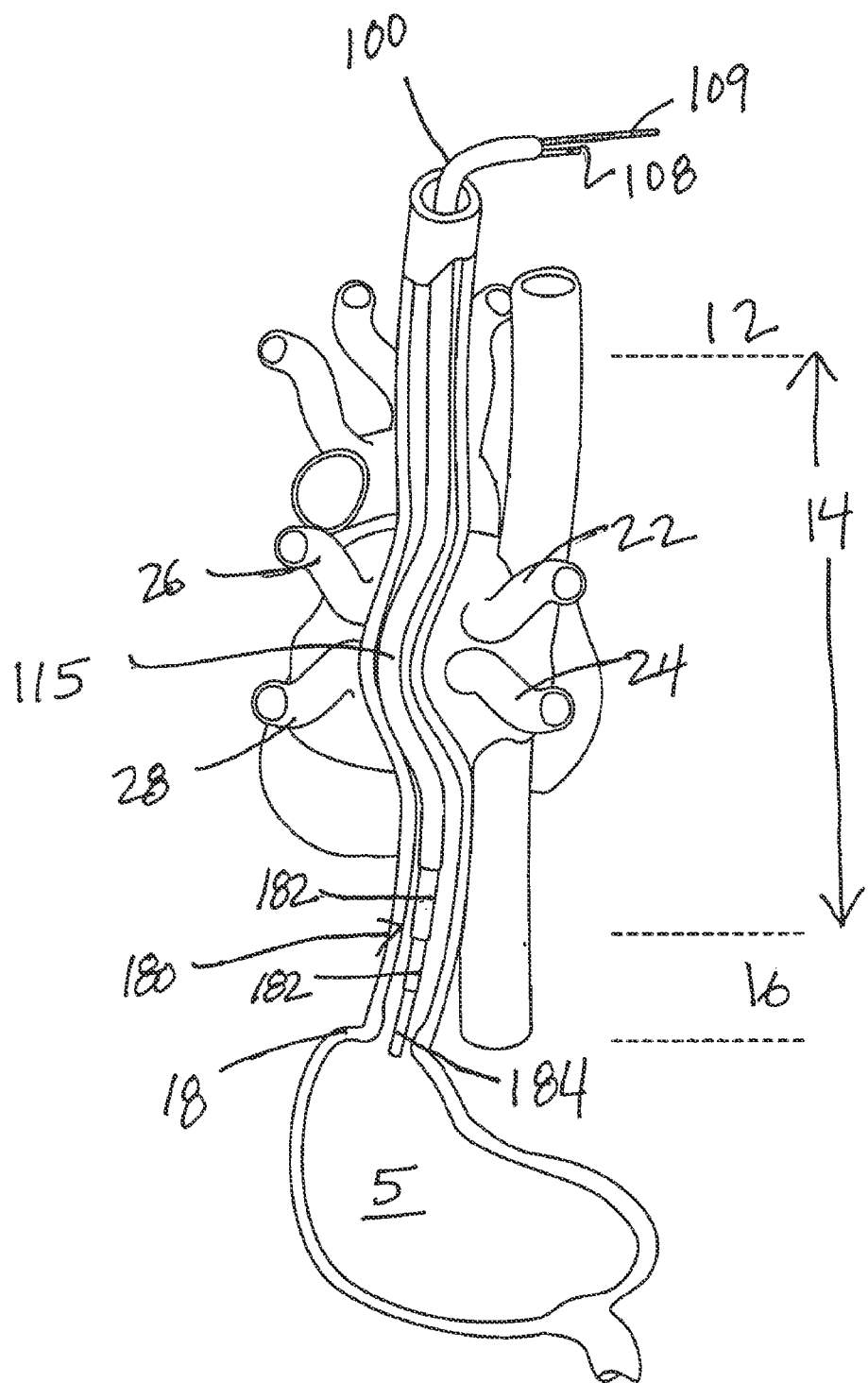
FIG. 7 is a posterior section view of the thoracic portion of the body with an apparatus to move the esophagus having a telescoping member with a plurality of telescoping sections, the apparatus is shown in place and moving the esophagus.

The use of suction as previously described is one way to ensure esophagus movement. Other techniques are possible to aid a user in ensuring that the esophagus bends in the intended manner. One other technique would be to anchor the apparatus 100 within the esophagus or provide an adjustable length beyond the controllable section 115. FIG. 7 is a posterior section view of the thoracic portion of the body with an apparatus to move the esophagus having a telescoping member 180. The telescoping member includes a plurality of telescoping sections 182. Optionally, the distal most section 184 may be inflatable. The section 184 may remain uninflated for transport to the esophagus and then may be inflated when anchoring is desired. Alternatively, instead of inflation, any other suitable technique for maintaining the section 184 in a stowed condition may be used during movement to the esophagus. Thereafter, if anchoring is desired, the section 184 may be suitably transitioned into a deployed position to anchor the distal portion of the apparatus within the esophagus 10 or the esophageal sphincter 18.

Figure 8A:
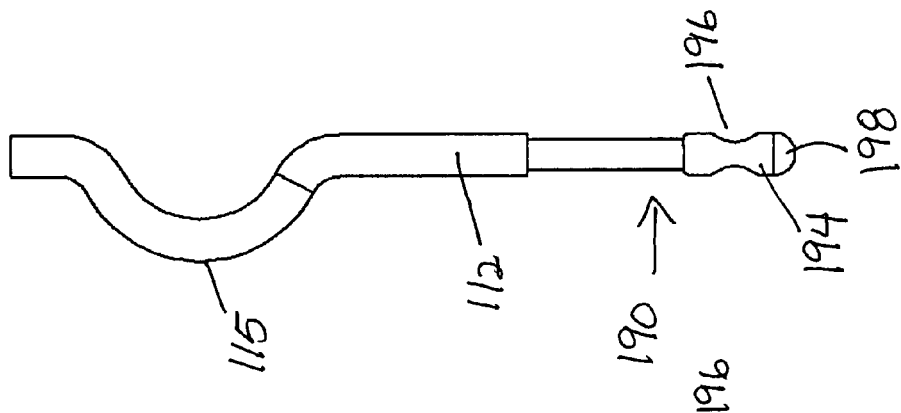
FIGS. 8A, 8B and 8C illustrate section views of an apparatus to move the esophagus having an alternative telescoping member and a distal anchor. The telescoping member is stowed or unextended in FIG. 8A, partially extended in FIG. 8B and fully extended in FIG. 8C.
Figure 8B:
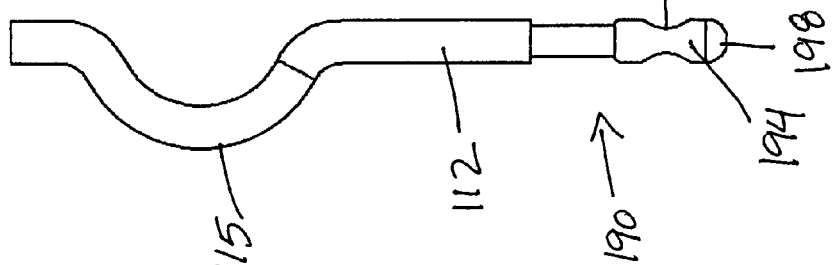
Figure 8C:
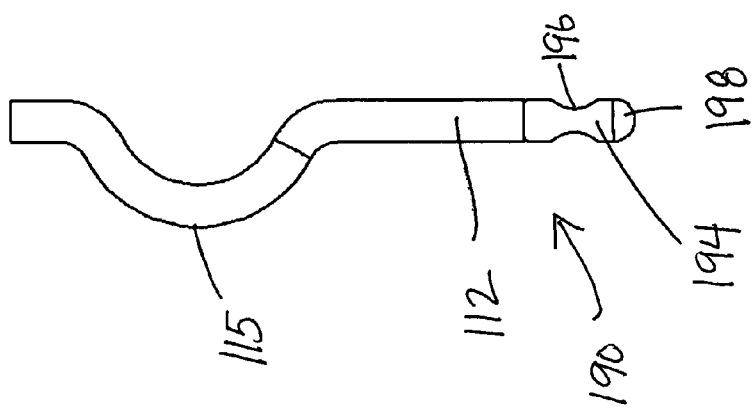
Figure 11:
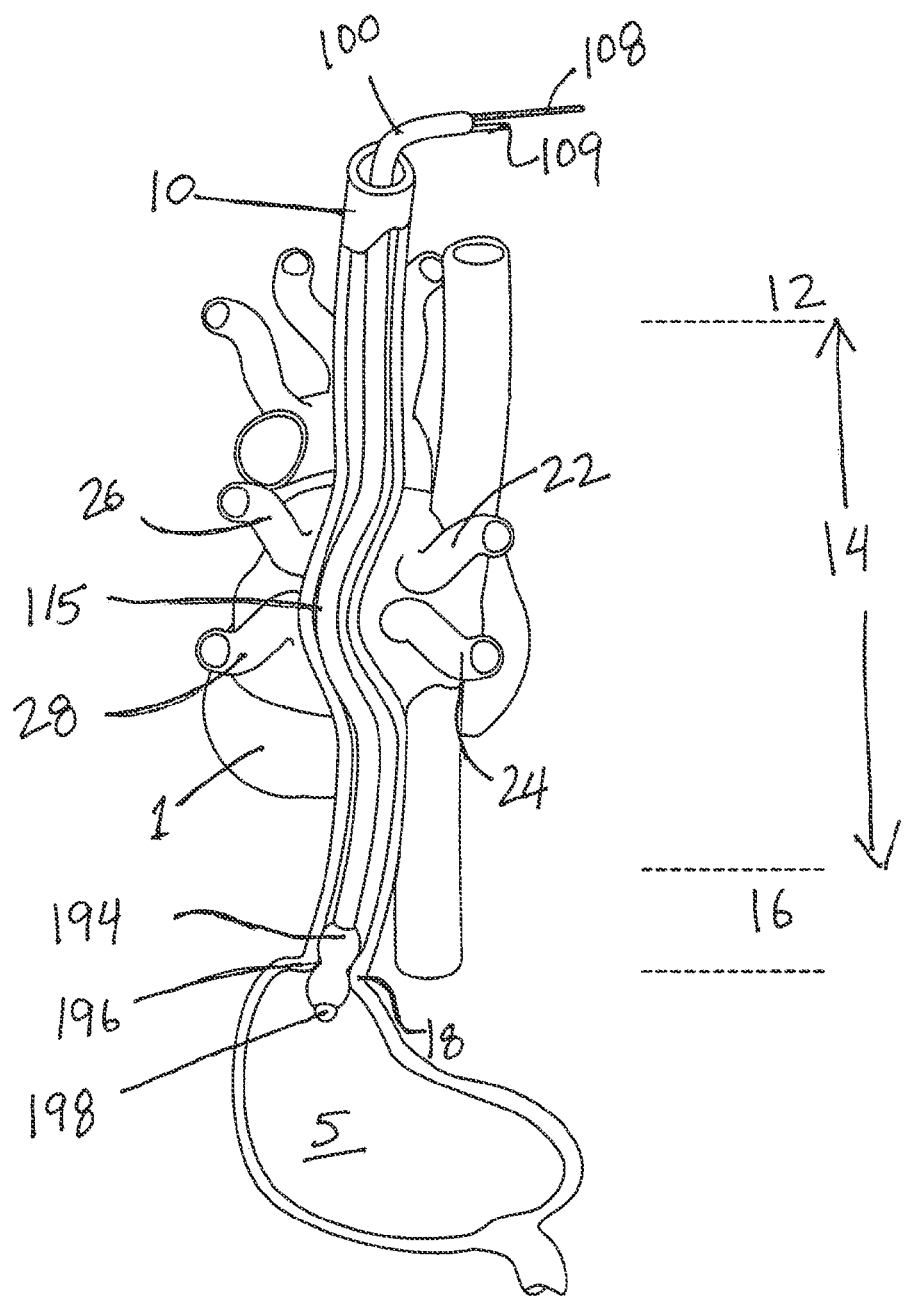
FIG. 11 is a posterior section view of the thoracic portion of the body with the apparatus of FIG. 10 with the anchor deployed within the esophageal sphincter and the apparatus moving the esophagus.

FIGS. 8A, 8B and 8C illustrate section views of an apparatus to move the esophagus having an alternative telescoping member 190 and a distal anchor 194. The telescoping member 190 is stowed or unextended in FIG. 8A, partially extended in FIG. 8B and fully extended in FIG. 8C. The distal anchor 194 has a tip 198 and groove 196. The anchor 194 may be shaped as a bulb (as illustrated) adapted to engage with the esophageal sphincter 18 as best seen in FIG. 11.

Returning to FIGS. 8A, 8B and 8C. In use, the anchor 194 engages with the esophageal sphincter 18 to secure the distal end of the apparatus 100 within the esophagus 10. Next, the elongate body 105 is withdrawn proximally until the section 115 is aligned with the portion of the esophagus to be moved. In this way, the telescoping member 190 provides a stable base to support movement of the esophagus in combination with the ability to adjust section 115 position relative to the esophageal sphincter 18 or other anchor location. This adjustment allows the apparatus to accommodate a wide range of anatomical variation. This variation includes, for example, differences in esophagus lengths or portions found between adults and children as well as between men and women.

The depth and shape of the groove 196 are adapted and configured to seat within the esophageal sphincter 18. The anchor 194 could be sized to pass through the mouth or nasal passage and also engage with the esophageal sphincter 18. Alternatively, the anchor 194 could be configurable into a stowed condition of sufficiently small size to pass through the mouth and nasal passage. Thereafter, the anchor 194 could be configured into a deployed condition of appropriate size for anchoring within the esophagus or the esophageal sphincter 18. After use, the anchor 194 may return to the stowed condition for removal. One example of a stowed condition is an inflatable anchor 194 that is uninflated. A corresponding example of a deployed condition would be to inflate the anchor 194.

Embodiments of the present invention having distal telescoping capability may also be adapted to include other controlled curvature functionality described herein. FIG. 9A is an isometric view of the apparatus to move the esophagus in FIG. 8A showing additional internal section components to add cooling capability to the controlled curvature section as described herein. FIG. 9B is an isometric view of the apparatus to move the esophagus in FIG. 8A showing additional section variations to add suction capability to the controlled curvature section as described herein. FIG. 9C is an isometric view of the apparatus to move the esophagus in FIG. 8A showing additional internal section components to add both cooling and suction capability to the controlled curvature section as described herein.

Figure 10:
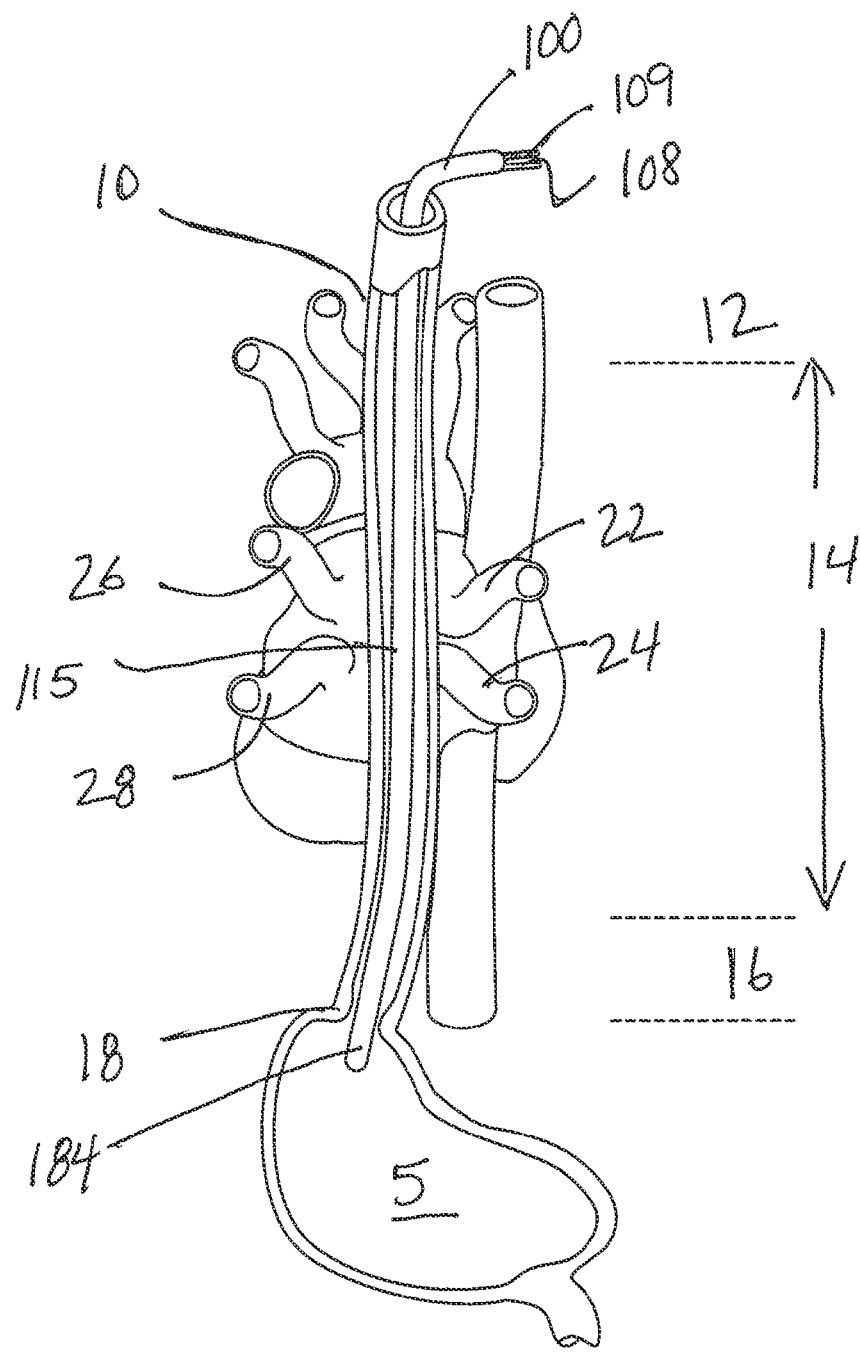
FIG. 10 is a posterior section view of the thoracic portion of the body with an apparatus to move the esophagus having a distal anchor. The apparatus is shown in place within the esophagus prior to deployment of the distal anchor.

FIG. 10 is a posterior section view of the thoracic portion of the body with an apparatus to move the esophagus having a distal anchor 184. The apparatus is shown in place within the esophagus prior to deployment of the distal anchor 184. When deployed, the anchor 184 engages with esophageal sphincter 18. The deployed condition may appear as illustrated in FIG. 11. FIG. 11 is a posterior section view of the thoracic portion of the body with the apparatus of FIG. 10 with the anchor 184 deployed within the esophageal sphincter 18. FIG. 11 illustrates an example of lateral medial movement of the esophagus. The movement illustrated in FIG. 11 may also include an anterior posterior curvature of the esophagus. Alternatively, the anchor 184 may be positioned instead in the abdominal portion 16 or the thoracic portion 14 to facilitate bending the esophagus with section 115.

Figure 12C:
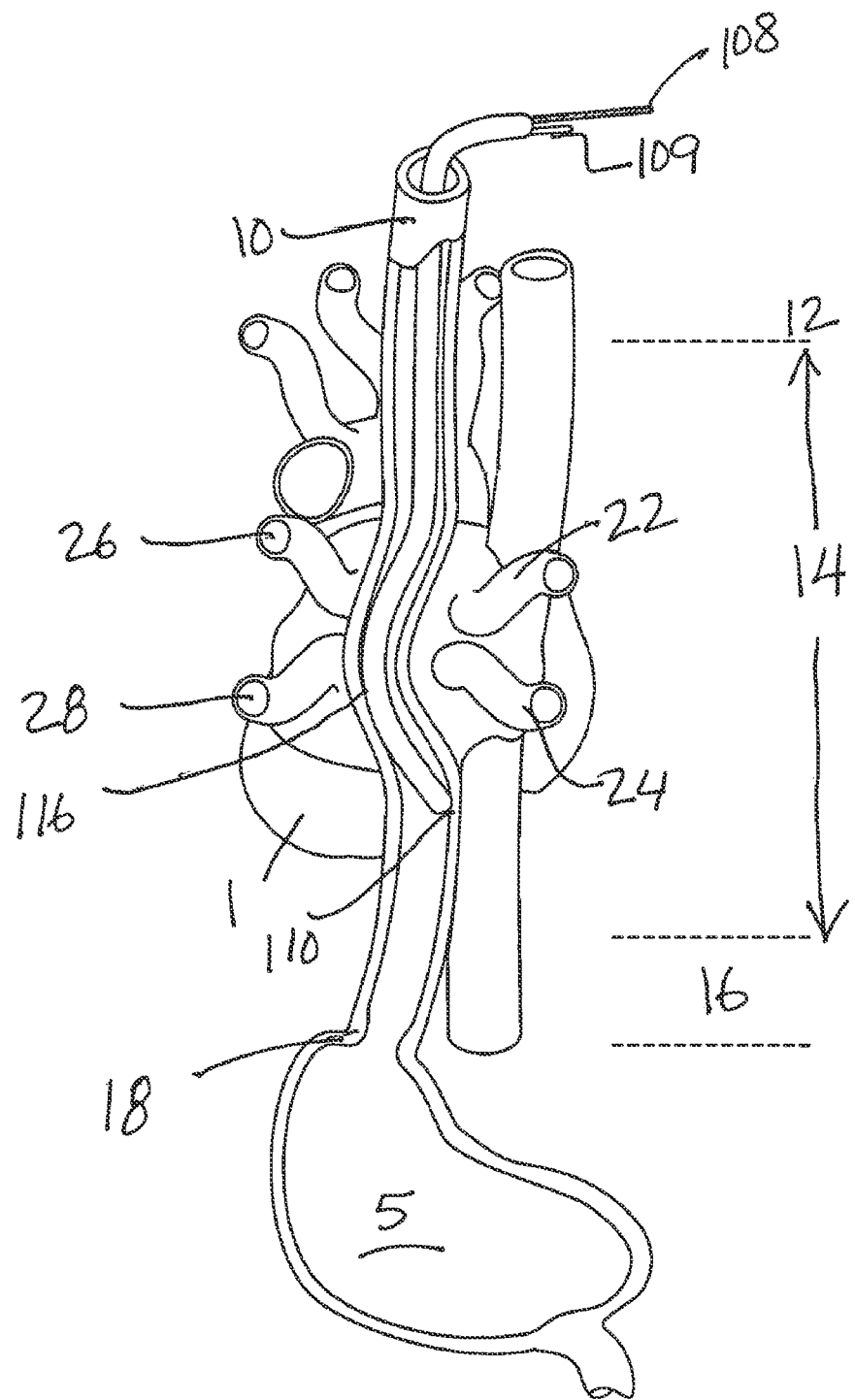
FIG. 12C is a posterior section view of the thoracic portion of the body with the device of FIG. 12A in place in, applying cooling to and moving the esophagus away from a therapy site near the right PVs.

FIG. 12A is an isometric view of a controlled curvature section 116 exposed to show the internal section components to add cooling capabilities. FIG. 12B is an exploded view of the controlled curvature section 116 in FIG. 12A showing the internal section components. A cooling unit insert 170 is adapted to be placed within the central portion 166 of the body 160. The cooling unit insert 170 includes conventional components to circulate medical grade cooling fluids within the section 116. Supply and return line connection 174, 176 are routed thought a manifold 172 to a cooling sleeve 178. In an alternative embodiment, all or portions of the components illustrated in FIG. 12B may be modified to increase thermal conductivity. One modification would be to make all or a portion of the components illustrated in FIG. 12B from a material having high thermal conductivity. Another modification would be to coat all or a portion of the controllable curvature section 116 with a material having high thermal conductivity. Another modification would be to coat all or a portion of the body 160 with a material having high thermal conductivity. Yet another modification would be to coat all or a portion of the sleeve 178 or cooling insert 170 with a material having high thermal conductivity. Exemplary materials include, but are not limited to: stainless steel, gold, aluminum, titanium, silver, and copper. Additional lines (not shown) extend through the elongate body 105 and connect manifold 172 to a conventional pumping system suited to circulating medical grade cooling fluids. In an alternative embodiment, the body 160 is not used and the sleeve 178 is placed directly with the section 116. In this embodiment, portions of the inner wall of section 116 may be modified to increase thermal conductivity. One modification would be to coat all or a portion of the controllable curvature section 116 with a material having high thermal conductivity. Exemplary materials include, but are not limited to: stainless steel, gold, aluminum, titanium, silver, and copper. The sleeve 178 may be placed on one side or to only cool a portion of the section 116 and then that cooled section may be positioned to provide cooling to the desired location. In another alternative, the sleeve 178 cools the entire section 116. FIG. 12C is a posterior section view of the thoracic portion of the body with the device of FIG. 12A in place in, applying cooling to and moving the esophagus away from a therapy site near the right pulmonary veins 22, 24.

Figure 13:
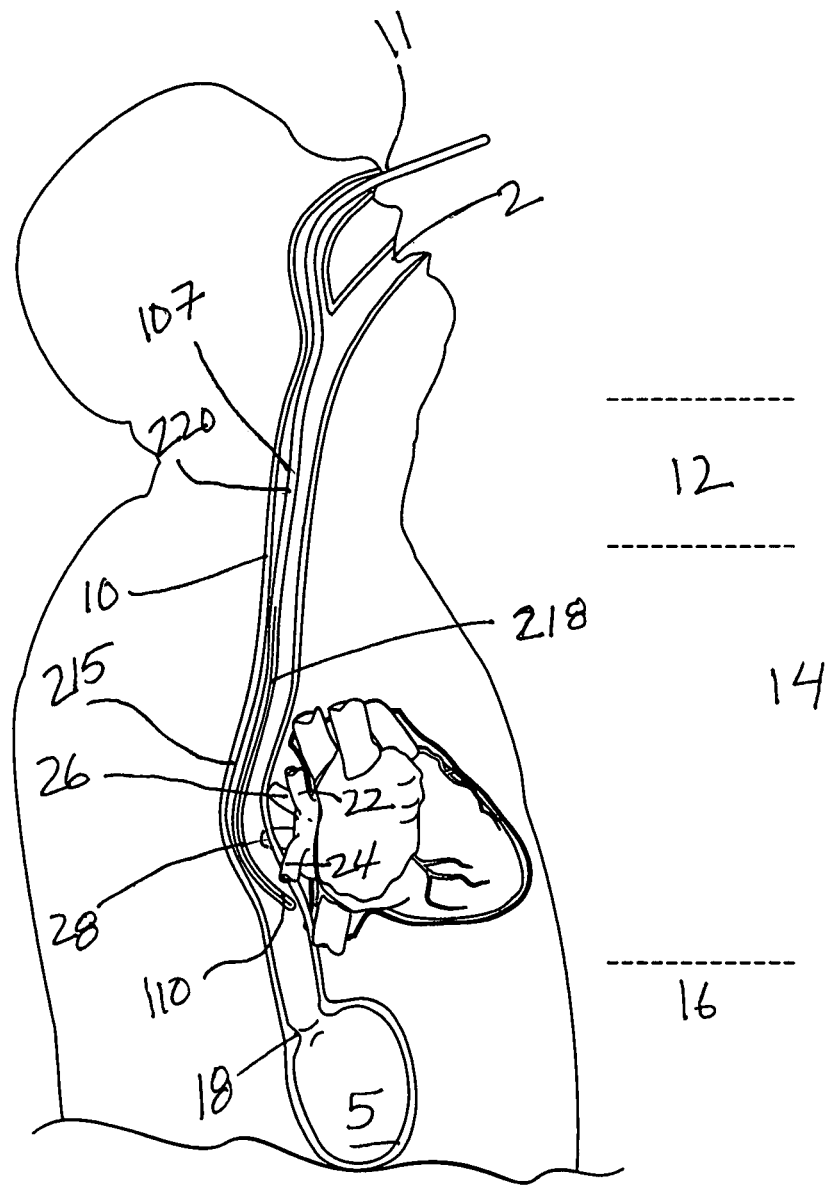
FIG. 13 is a section view of an apparatus adapted to pass through the nasal passage and move the esophagus. The apparatus is shown in place the thoracic portion of the body and moving the esophagus.

FIG. 13 is a section view of an apparatus 107 adapted to pass through the nasal passage 11 and move the esophagus 10. The apparatus 107 is shown in place the thoracic portion of the body and moving the esophagus 10. In one embodiment, apparatus 107 is provided with a handle (not shown) and is configured as described herein but only modified to also fit through the nasal passage. In an alternative, the apparatus 107 does not have a handle but instead is bent by imparting a local force to the curvature section 215. In this embodiment, the apparatus 107 for moving the esophagus has a flexible elongate body having a distal tip 110, a controlled curvature section 215, and a proximal section 220. The apparatus 107 also includes a bendable element 218 within the controlled curvature section 215 that, when bent, move and hold controlled curvature section 215 into a corresponding bent shape. In one embodiment, the bendable element 218 is a wire. In another embodiment, the bendable element 218 extends along the length of the proximal section 220. In another embodiment, the length of the controlled curvature section 215 is less than the length of the thoracic portion 14 of the esophagus 10.

This manual version of the apparatus to bend the esophagus may be used to bend any portion of the esophagus. For example, during an open chest procedure, a user may place the apparatus 107 into the esophagus via nasal passage (as shown) or alternatively, though the mouth. Then, in order to move the esophagus, the user simply bends both the esophagus and the apparatus 107 together. The one or more bendable elements 218 within the controlled curvature section 215 may be any suitable wire, strands, tendons, cables or other elements within the apparatus 107 capable of: (a) holding the user imposed curvature and (b) hold the esophagus in the user imposed position.

In one embodiment, the apparatus is designed for the prevention of esophageal damage as a result of RF ablation energy applied to the posterior wall of the LA. In another embodiment, the apparatus moves while simultaneously cooling the lumen of the esophagus at a constant temperature. Hence, it is designed to not only increase the distance between the sites of RF delivery but it is also designed to provide real-time control of the esophagus's temperature. One or more temperature probes may be placed along the length of the apparatus, in a radial array on the apparatus, grouped within a portion of the apparatus or in any other arrangement for measuring and indicating the temperature of the esophagus.

The fabrication techniques and materials used in steerable catheters are applicable to the fabrication techniques and materials used in the devices to move the esophagus according to the present invention. Similarly, the techniques and mechanisms used to steer the distal tip of a steerable catheter may also be used to impart curvature to the various controlled curvature sections of the present invention.

While there are similarities, the teachings of the steerable catheter arts are modified in several key aspects for application to the esophagus movement devices described herein. In contrast to steerable catheters, bending occurs in a controlled curvature section proximal to the tip, not in tip itself Additionally, the controlled curvature section is more rigid than the surrounding tissue when the curvature is formed. Catheter tips must be less rigid to operate properly and safely. A rigid steerable catheter tip could lead to an inability to follow the desired vessel pathway or/and lead to the puncturing the vessel if improperly bent. In much the same way, the catheter is designed to move within and follow the lumen it is within and not bend or contort the vessel. In contrast, the controlled curvature section is designed and positioned to bend the surrounding esophagus. Unlike catheters that transit the vasculature with associated size restrictions, the diameter of esophagus movement devices may be as large as the inner diameter of the esophagus and completely fill the esophagus while remaining within the size constraints of fitting through the mouth or the nasal passage. Most importantly, instead of merely deflecting the tip of an instrument, the devices described herein bend a controlled curvature section that is long as or almost as long as the thoracic portion of the esophagus. In view of the above differences, the following steerable catheter patents are incorporated by reference in their entirely for all purposes: U.S. Pat. No. 3,773,034, U.S. Pat. No. 4,960, 411, U.S. Pat. No. 5,090,956 and U.S. Pat. No. 5,125,895.

One or more bending mechanisms and or locking mechanisms may be used in combination. Additionally, for simplicity, section 115 was shown bending within a single plane with simple curved shape within a single plane. It is to be appreciated that the section 115 may be configured and adapted to produce compound shapes and irregular shapes. In addition, multiple means for adjusting the curvature of the section 115 may be used to produce compound curves. The means for adjusting may be aligned such that, when activated by a mechanism in the handle, a bend, curve or alteration of the section occurs within a given plane. For example, one adjusting means may be used to provide lateral medial movement while another provides anterior posterior movement. Alternatively, the adjusting means may be aligned to section 115 to impart curvature of the esophagus in relation to the anatomical planes: the coronal, sagittal and transverse planes. In another alternative embodiment, a single means for adjusting the curvature of the section 115, in use, produces a curve within more than one anatomical plane.

In other embodiments, components of the apparatus 100 may be formed from or include radio opaque materials. For example, any of the tip, the controlled curvature section or the flexible section may include a radio opaque marker. Suitable materials for adding radio opaque characteristics include, for example, poly-urethane and poly-vinyl-chloride.

We claim:

1. A method of adjusting the curvature of the esophagus of a human being during a therapeutic procedure in a treatment area outside of the esophagus, comprising:
positioning within the esophagus an elongate body having a distal tip, a controlled curvature section having a length that is less than the length of the thoracic portion of the esophagus, a first flexible section proximal to the controlled curvature section, a second flexible section distal to the controlled curvature section, and a telescoping section distal to the controlled curvature section;
anchoring a distal portion of the telescoping section within the esophagus;
withdrawing the controlled curvature section proximally to extend the telescoping section from within the second flexible section to place at least a portion of the controlled curvature section within the thoracic esophagus; and
adjustably controlling the curvature of the controlled curvature section to increase the distance between the esophagus and a treatment area outside of the esophagus without adjustably controlling the curvature of the first flexible section and second flexible section.

2. The method of adjusting the curvature of the esophagus according to claim 1 further comprising: engaging the interior wall of the esophagus with the outer wall of the controlled curvature section.

3. The method of adjusting the curvature of the esophagus according to claim 1 further comprising: cooling the interior wall of the esophagus with the controlled curvature section.

4. The method of adjusting the curvature of the esophagus according to claim 1, the anchoring the distal portion of the telescoping section within the esophagus step comprising: positioning a bulb on the telescoping section within the esophageal sphincter.

5. The method of adjusting the curvature of the esophagus according to claim 4 wherein positioning a bulb into the esophageal sphincter comprises: deploying the bulb to engage with the esophageal sphincter.

6. The method of adjusting the curvature of the esophagus according to claim 1 the adjustably controlling step further comprising: increasing the distance between the esophagus and an ablation site.

7. The method of adjusting the curvature of the esophagus according to claim 1 the adjustably controlling step further comprising: creating an anterior posterior curvature within the esophagus.

8. The method of adjusting the curvature of the esophagus according to claim 1 the adjustably controlling step further comprising: creating a lateral medial curvature within the esophagus.

9. The method of adjusting the curvature of the esophagus according to claim 1 the adjustably controlling step further comprising: controlling the curvature of the controlled curvature section by adjusting a mechanism on a handle attached to the elongate body.

10. The method of adjusting the curvature of the esophagus according to claim 1 the adjustably controlling step further comprising: using a locking device to lock the position of the controlled curvature section.

11. The method of adjusting the curvature of the esophagus according to claim 1 the adjustably controlling step further comprising: controlling the curvature of the controlled curvature section by adjusting a bendable element disposed within the controlled curvature section.

12. The method of claim 1, wherein the controlled curvature section is configured to assume a plurality of different curvatures, and wherein adjustably controlling the curvature comprises adjusting the curvature to one curvature of the plurality of different curvatures.

* * * * *